(12) United States Patent
Onisko et al.

(10) Patent No.: US 8,445,642 B1
(45) Date of Patent: May 21, 2013

(54) METHODS TO DIFFERENTIATE PROTEIN CONFORMERS

(75) Inventors: Bruce C. Onisko, Kensington, CA (US); Christopher J. Silva, Albany, CA (US); Jesus R. Requena, Briom (ES); John Mark Carter, Richmond, CA (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 519 days.

(21) Appl. No.: 12/251,456

(22) Filed: Oct. 14, 2008

Related U.S. Application Data

(63) Continuation-in-part of application No. 11/249,216, filed on Oct. 13, 2005, now abandoned.

(51) Int. Cl.
*C07K 16/00* (2006.01)
*C07K 16/06* (2006.01)
*C07K 16/18* (2006.01)

(52) U.S. Cl.
USPC ....... 530/387.1; 530/388.1; 435/2; 424/184.1

(58) Field of Classification Search
None
See application file for complete search history.

(56) References Cited

U.S. PATENT DOCUMENTS

| | | | |
|---|---|---|---|
| 5,108,900 A * | 4/1992 | Stanker et al. | 435/7.93 |
| 6,660,843 B1 * | 12/2003 | Feige et al. | 530/391.7 |
| 2002/0123072 A1 * | 9/2002 | Prusiner et al. | 435/7.1 |

* cited by examiner

*Primary Examiner* — Michelle S Horning
(74) *Attorney, Agent, or Firm* — Elizabeth Sampson; Lesley Shaw; John D. Fado

(57) ABSTRACT

The invention is directed to methods to distinguish among different protein conformers of the same protein such as proteins which form amyloid deposits. Using the methods of the invention, one or more protein conformers in a sample can be detected, differentiated, and quantitated. An example of a protein which is known to exist in at least two conformations is the normal prion protein ($PrP_C$) and its infectious isoform ($PrP^{Sc}$). The invention provides means to distinguish $PrP^C$ from $PrP^{Sc}$ and allows quantitation of each individually, even when the conformers are present together in a mixture. Thus, the methods of the invention can provide important tools for human and animal health.

6 Claims, 7 Drawing Sheets

SEQUENCE LISTING

<160> NUMBER OF SEQ ID NOS: 1

<210> SEQ ID NO 1
<211> LENGTH: 146
<212> TYPE: PRT
<213> ORGANISM: Syrian Hamster

<400> SEQUENCE: 1

```
Gly Gly Gly Trp Gly Gln Gly Gly Thr His Asn Gln Trp Asn Lys
1               5                   10                  15

Pro Ser Lys Pro Lys Thr Asn Met Lys His Met Ala Gly Ala Ala Ala
            20                  25                  30

Ala Gly Ala Val Val Gly Gly Leu Gly Gly Tyr Met Leu Gly Ser Ala
            35                  40                  45

Met Ser Arg Pro Met Met His Phe Gly Asn Asp Trp Glu Asp Arg Tyr
        50                  55                  60

Tyr Arg Glu Asn Met Asn Arg Tyr Pro Asn Gln Val Tyr Tyr Arg Pro
65                  70                  75                  80

Val Asp Gln Tyr Asn Asn Gln Asn Asn Phe Val His Asp Cys Val Asn
                    85                  90                  95

Ile Thr Ile Lys Gln His Thr Val Thr Thr Thr Thr Lys Gly Glu Asn
                100                 105                 110

Phe Thr Glu Thr Asp Ile Lys Ile Met Glu Arg Val Val Glu Gln Met
            115                 120                 125

Cys Thr Thr Gln Tyr Gln Lys Glu Ser Gln Ala Tyr Tyr Asp Gly Arg
        130                 135                 140

Arg Ser
145
```

METHODS TO DIFFERENTIATE PROTEIN CONFORMERS

RELATED APPLICATIONS

This application is a Continuation-in-Part (CIP) of U.S. patent application Ser. No. 11/249,216, filed Oct. 13, 2005 now abandoned. This application claims priority to co-pending U.S. patent application Ser. No. 11/249,216 which is incorporated herein by reference in its entirety.

BACKGROUND OF THE INVENTION

1. Field of the Invention

The present invention relates to methods for detecting one or more protein conformers in a sample containing a protein having at least two protein conformations. Thus, the invention is directed to methods for distinguishing and quantitating stable protein conformations of the same protein. An example of a protein which is known to exist in at least two conformations is the normal prion protein ($PrP^C$) and its infectious isoform ($PrP^{Sc}$).

2. Description of the Art

The vast majority of proteins adopt only one stable conformation, however, exceptions exist. Indeed, in recent years it has come to light that many proteins can adopt more than one stable folded conformation that is they have multiple isoforms or conformers. Interestingly, a number of the proteins having multiple isoforms are important agents of disease see e.g., Citi, F., and Dobson, C. M. (2006) Ann. Rev. Biochem. 75:333-366 and Wickner R B., et al. (2008) Bioessays. 2008; 30:955-64.

At least sixteen types of human disease are associated with fibrils made of abnormally folded proteins (see e.g., Pepys (1996) *Amyloidosis*. In Weatherhall, D. J, Ledingham, J. G. G. and Warell, D. A. (Eds), *The Oxford Textbook of Medicine*, 3rd edition, Vol 2, Oxford University Press, Oxford, UK, 1512-1524). For example, amyloid fibrils are associated with diseases including, but not limited to spongiform encephalopathies, Alzheimer's disease, Parkinson's disease, Hunington's disease, and type II diabetes.

An example of a protein which causes disease when misfolded is the prion protein. Prions, such as mammalian PrP and fungal sup35, are unique amongst amyloidogenic proteins in that they are known to exist in more than two stable conformations. Prion diseases have properties that are maintained upon transmission from one host to the next, allowing different prion "strains" to be distinguished. The strains cause specific phenotypes, such as different symptomology (ataxias, hyperactivity, lethargy), time from exposure to disease, and different tissue distribution of $PrP^{Sc}$.

A critical difference between prions and other amyloids is that prions are by definition infectious (see e.g., Prusiner (1982) *Science* 216(9):136-144). Very substantial and diverse evidence suggests that transmissible spongiform encephalopathies (TSEs), a group of fatal neurodegenerative diseases affecting humans and animals, are mediated by a prion, named PrP (prion protein) (see e.g., Prusiner (1982) supra; Prusiner (1998) *Proc. Natl. Acad. Sci.* 95:13363-13383; Soto and Castilla (2004) *Nat. Med.* 7 Suppl. S63-S67; Aguzzi and Polymenidou (2004) *Cell* 116:313-327; and Prusiner (1991) *Science* 252:1515-1522). The most widely studied TSEs in food-producing animals include scrapie in sheep and goats, bovine spongiform encephalopathy (BSE) in cattle, and chronic wasting disease (CWD) in mule deer and elk. Other TSEs in animals included transmissible mink encephalopathy (TME) in mink and feline spongiform encephalopathy (FSE) of cats. Prion diseases of humans have also been identified. These include: Creutzfeldt-Jakob Disease (CJD); Gerstmann-Straussler-Scheinker Syndrome (GSS); Fatal Familial Insomnia (FFI), and Kuru.

PrP exists in at least two conformations, $PrP^C$ and $PrP^{Sc}$. The latter is associated with TSEs, and PrP showing the physico-chemical characteristics of $PrP^{Sc}$ is isolated as the main and most probably only component of the TSE infectious agent. $PrP^C$ can be converted into $PrP^{Sc}$, in the presence of pre-formed $PrP^{Sc}$, through a poorly understood molecular process (see e.g., Aguzzi and Polymenidou (2004) supra; Prusiner (1991) supra; and Come et al. (1993) *Proc. Natl. Acad. Sci.* 90:5959-5936). The structure of $PrP^C$ has been characterized by NMR (see e.g., Riek et al. (1996) *Nature* 382:180-182), but that of $PrP^{Sc}$ is largely unknown, as its insolubility in non-denaturing solvents has seriously hampered analytical efforts. It is known, however, that $PrP^{Sc}$ and $PrP^C$ differ with respect to secondary, tertiary and quaternary structures (see e.g., Prusiner (1998) supra). No covalent differences have been detected between the two molecules (see e.g., Stahl et al. (1993) *Biochemistry* 32:1991-2002), although the possibility that post-translational modifications of a small set of $PrP^C$ molecules could trigger structural changes relevant to initiation of conversion to $PrP^{Sc}$ cannot be ruled out (see e.g., Requena et al. (2001)). Studies using Fourier transform infrared spectroscopy (FTIR) indicate that $PrP^{Sc}$ contains an increased fraction of β-sheet and decreased fractions of α-helix and random coil with respect to $PrP^C$ (see e.g., Prusiner (1998) supra). $PrP^C$ is a monomeric protein anchored to the cell membrane through a glycan phosphoinositol (GPI) anchor. In contrast, $PrP^{Sc}$ is isolated as an aggregate. $PrP^{Sc}$ is partially resistant to proteinase K (PK), that trims an amino terminal segment of the protein generating a well defined resistant core termed PrP 27-30 whereas $PrP^C$ is rapidly degraded by PK (see e.g., Prusiner (1998) supra). PrP 27-30 retains the infectious character, and hence the essential structural characteristics, of $PrP^{Sc}$, with the trimmed amino-terminal domain probably consisting of a highly flexible tail as seen in $PrP^C$. In the presence of detergent, PrP 27-30 further polymerizes to rod-shaped filaments with the tinctorial properties of amyloid (see e.g., McKinley et al. (1991) *J. Virology* 65(3): 1340-1351).

At present, protein conformers can be discriminated by methods such as (FTIR) or circular dichroism (CD) spectroscopy, but only when the proteins have been extensively purified. NMR and X-ray diffraction, the most common methods to determine protein structure, have been used successfully to determine the three dimensional structure of the soluble forms of amyloidogenic proteins (e.g., the cellular form of the prion protein $PrP^C$), however these methods can not be used for the amyloids themselves since amyloids by nature are neither soluble, as required by NMR, nor crystallizable, as required by high resolution X-ray diffraction.

Considerable effort has gone towards attempts to find antibodies that discriminate $PrP^{Sc}$ from $PrP^C$ but to date, no antibodies have been found that selectively bind $PrP^{Sc}$ see e.g., Gibbs C J, Gajdusek D C, Morris J A. *Viral characteristics of the scrapie agent in mice*. In: Gajdusek C J, Gibbs C J, Alpers M P, eds. Slow, Latent, and Temperate Virus Infections. Washington, D. C.: U.S. Government Printing Office; 1965: 195-202; Porter D D, Porter H G, Cox N A. (1973) *J Immunol.* 111:1407-1410; Prusiner, S. B. Prions: (1984) Adv. Virus. Res. 29:1-56; Gardash'yan, A M, Nartsissov N V, and Bobkova O V. (1971) Bull. Exp. Biol. Med. 1971; 71: 664-666; Moulton J E, Palmer A C. (1959) Cornell Vet. 49:349-359; Gardiner A C. (1966) Res Vet Sci. 1966; 7: 190-195; Chandler R L. Vet Rec. (1959) 71:58-59; Pattison I H, Millson G C, Smith K. (1964) Vet. Sci. 1964; 5: 116-121; Clarke M C, Haig D A. (1966) Vet. Rec. 78:647-649; Gibbs C J Jr. (1967) Curr. Top. Microbiol. Immunol. 40:44-58.

In view of the considerable human and animal health considerations related to alternately folded proteins that form amyloid deposits, what is needed are methods to detect, distinguish, and, if desired, quantitate two or more protein conformations of the same protein.

SUMMARY OF THE INVENTION

The invention comprises methods to distinguish among different protein conformers of the same protein such as proteins which form amyloid deposits. Using the methods of the invention, one or more protein conformers in a sample can be detected, differentiated, and quantitated. Thus, for example, in the case of prion protein conformers, the method provides a means to distinguish $PrP^C$ from $PrP^{Sc}$ and allows quantitation of each individually, even when the conformers are present together in a mixture. Because the methods of the invention distinguish among conformers, samples having only one protein conformer can be identified. This is useful to identify the presence of amyloid diseases in humans or animals. Thus, the methods of the invention can provide important tools for human and animal health.

In an exemplary embodiment, the method of the invention for detecting, distinguishing or quantitating a protein conformer in a sample comprising a protein having a plurality of protein conformers, wherein each conformer is characterized by a unique protein conformation, comprises:

(a) reacting the sample with a protein-modifying reagent which reacts differentially with each of the plurality of protein conformers under conditions whereby the reagent forms one or more covalent bonds with a first one of the plurality of protein conformers to form a first unique entity, and a second entity corresponding to each additional protein conformer results either because the reagent does not form a covalent bond or bonds with a second one of the plurality of protein conformers or because the reagent forms a covalent bond or bonds with a second one of the plurality of protein conformers wherein the covalent bond or bonds is or are different from the covalent bond or bonds formed with the first protein conformer; and (b) analyzing the reacted sample of step (a) to determine the presence of the unique modified peptide of the first entity or to determine the presence of the unique different peptide of the second entity.

In another exemplary embodiment, the method of the invention for detecting, distinguishing or quantitating a protein conformer in a sample comprising a protein having a plurality of protein conformers, wherein each conformer is characterized by a unique protein conformation, comprises:

(a) reacting the sample with a protein-modifying reagent which reacts differentially with each of the plurality of protein conformers under conditions whereby the reagent forms one or more covalent bonds with a first one of the plurality of protein conformers to form a first unique entity, and a second entity corresponding to each additional protein conformer results either because the reagent does not form a covalent bond or bonds with a second one of the plurality of protein conformers or because the reagent forms a covalent bond or bonds with a second one of the plurality of protein conformers wherein the covalent bond or bonds is or are different from the covalent bond or bonds formed with the first protein conformer;

(b) treating the reacted sample of step (a) with a protein-cleaving reagent under conditions whereby a peptide bond or bonds in the first entity is cleaved to form at least one unique modified peptide and whereby a peptide bond or bonds in the reacted second entity is cleaved to form a unique different peptide which differs from the unique modified peptide of the first entity; and (c) analyzing the treated sample of step (b) to determine the presence of the unique modified peptide of the first entity or to determine the presence of the unique different peptide of the second entity.

In some exemplary embodiments, the methods further comprise the steps of analyzing for both the unique modified peptide of the first entity and the presence of the unique different peptide of the second entity. The invention methods further encompass the embodiment wherein the plurality of protein conformers includes more than two and wherein one or more of the protein conformers is quantitated. The peptides may be analysed by various methods such as: Mass spectrometric, colorimetric, immunometric, fluorometric, or radiometric detectors with or without prior chromatographic separation.

Thus, in an exemplary embodiment one exemplary embodiment, the invention provides a means for distinguishing among protein conformers. Using the methods of the invention, chemical markers can be created that are unique to each conformer of the same protein, and the ratio or absolute amounts of each conformer can be determined.

The invention fulfills an important need of providing means to detect and distinguish different protein conformers of a protein such as one which forms amyloid deposits.

An example of a protein which is known to exist in at least two conformations is the normal prion protein ($PrP^C$) and its infectious isoform ($PrP^{Sc}$). $PrP^{Sc}$ is found in the brain of mammals infected with TSE diseases, such as CJD, BSE, CWD, TME, and scrapie. These conformers have different biological properties and are important to human health and animal health. They can be transmitted from person to person, animal to animal, and animal to people. Currently, there is no means of identifying asymptomatic carriers or infected, but asymptomatic people or animals. Thus, the ability to identify such persons or animals would be a benefit to human and animal health.

The invention provides an important public safety tool. There is considerable interest in methods to demonstrate the safety of beef and beef products worldwide. The methods of the invention fulfill the need of providing an assay to detect low levels of prions in live animals.

It is an object of the invention to enable the differentiation of proteins like $PrP^{Sc}$ that are known to exist in more than two conformers, colloquially known as "strains". The implications to agriculture of the different prion strains may be enormous. For example, the invention could be used to determine the etiology of TSE outbreaks or determine the genesis of new TSE strains.

Conformational difference may be a form of protein regulation, so distinguishing conformations may be used to identify conformers that regulate cellular processes. For example, cytosolic polyadenylation element binding protein exists in at least two conformations which are believed to have different biochemical properties. Distinguishing between conformations would allow the testing of this hypothesis, and further elucidate the mechanism of long term potentiation in neurons.

The differing reactivity of amino acid residues would allow the relative position of amino acids to be determined, thus giving structural information that is not obtainable from any other means and providing key information to assist modeling of protein structures that can not be studied by NMR spectrometry or X-ray diffraction.

Other objects and advantages of the invention will become readily apparent from the ensuing description.

DETAILED DESCRIPTION OF THE INVENTION

Figure 1:
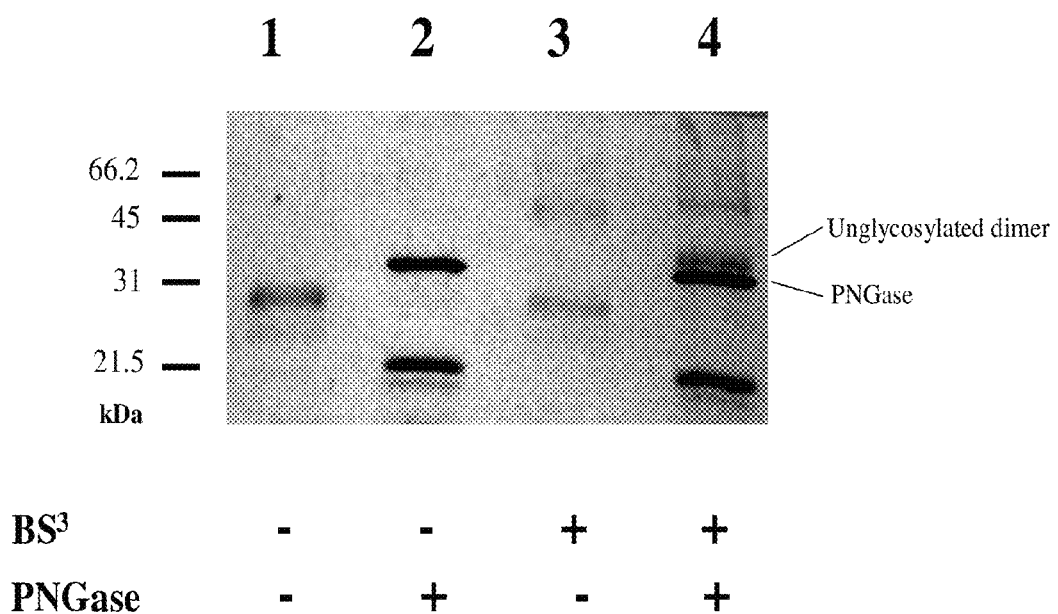
FIG. 1 shows cross-linking of PrP27-30 by $BS^3$. As discussed in detail in the Materials and Methods of Example 1, below, PrP27-30 was treated with 1.7 mM $BS^3$ at 37° C. for 30 minutes. The reaction was quenched with lysine and PrP 27-30 submitted to SDS-PAGE with or without previous deglycosylation with PNGase F. The gel was stained with Coomassie blue.

In an exemplary embodiment, the invention is directed to methods to distinguish different stable conformations of the same protein. In another exemplary embodiment the invention is directed to methods wherein the distinguished conformations are also quantitated. Thus, using the methods of the invention, two or more different conformations of the same protein such as one which forms amyloid deposits can be distinguished from one another, and each one can be quantitated individually, even when present in a mixture.

DEFINITIONS

The term "protein" as used herein is intended to encompass any amino acid sequence and include modified sequences such as glycoproteins. The term includes naturally occurring proteins and peptides as well as those which are recombinantly or synthetically synthesized. As used in connection with the present invention the term "protein" is specifically intended to cover naturally occurring proteins which occur in at least two different stable macromolecular conformations wherein both conformations have the same or substantially the same amino acid sequence but have different three dimensional structures. The two conformations of the protein include at least one conformation which is not related to a disease state and at least one conformation which is related to a disease state—pathogenic. A specific and preferred example of a protein as used in connection with this disclosure is a PrP protein which includes the non-disease form referred to as the $PrP^C$ form and the disease related form referred as the $PrP^{Sc}$. Although a prion protein or the $PrP^{Sc}$ form of a PrP protein is infectious and pathogenic, the disease conformation of other proteins is not infectious although it is pathogenic. As used herein, the term pathogenic may mean that the protein actually causes the disease or it may simply mean that the protein is associated with the disease and therefore is present when the disease is present. Thus, a pathogenic protein as used in connection with this disclosure is not necessarily a protein which is the specific causative agent of a disease.

The term "conformer" or equivalently "isoform" as used herein, refers to proteins that have identical amino acid sequences but which have different three dimensional conformations.

The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three dimensional structural characteristics as well as specific charge characteristics.

The term "hapten" as used herein refers to molecules that are typically too small to generate an immune response on their own, but which react covalently with poorly immunogenic materials to form a "newly created epitope". Because the "newly created epitope" is very distinct from the unmodified poorly immunogenic material, the overall chemical structure is typically strongly recognized by the immune system as foreign. This allows the host immune system to render a robust response to the hapten in the form of a "newly created epitope".

The term "antibody" refers to a polypeptide encoded by an immunoglobulin gene, or functional fragments thereof that specifically recognizes and specifically bind and an epitope. Recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit has a tetrameric structure which comprises two identical pairs of polypeptide chains, each pair having one "light" (about 25 lcDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Exemplary antibody functional fragments include, but are not limited to, complete antibody molecules, antibody fragments, such as Fv, single chain Fv (scFv), complementarity determining regions (CDRs), $V_L$ (light chain variable region), $V_H$ (heavy chain variable region), Fab, F(ab)$_2$' and any combination of those or any other functional portion of an immunoglobulin peptide capable of binding to target hapten or target antigen (see, e.g., Fundamental Immunology (Paul ed., 3d ed. 1993).

As appreciated by one of skill in the art, various antibody fragments can be obtained by any variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol*:5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

References to "$V_H$" or a "VH" refer to the variable region of an immunoglobulin heavy chain, including an Fv, scFv, a disulfilde-stabilized $F_v$ (dsFv) or Fab. References to "$V_L$" or a "VL" refer to the variable region of an immunoglobulin light chain, including of an Fv, scFv, dsFv or Fab.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. The numbering of the light and heavy chain variable regions described herein is in accordance with Kabat (see, e.g., Johnson et al., (2001) "Kabat Database and its applications: future directions" *Nucleic Acids Research,* 29: 205-206; and the Kabat Database of Sequences of Proteins of Immunological Interest, Feb. 22, 2002 Dataset).

The positions of the CDRs and framework regions are determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.,* 28, 219-221 (2000); and Lefranc, M.-P. IMGT, the international ImMunoGeneTics database. *Nucleic Acids Res.* January 1; 29(1):207-9 (2001); MacCallum et al, Antibody-antigen interactions: Contact analysis and binding site topography, *J. Mol. Biol.,* 262 (5), 732-745 (1996); and Martin et al, *Proc. Natl. Acad. Sci. USA,* 86, 9268-9272 (1989); Martin, et al, *Methods Enzymol.,* 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

The term "hybridoma cell line" as used herein, refers to a permanent cell line derived from the fusion of a cultured a neoplastic lymphocyte (e.g. a mouse plasmacytoma cell) and specific antibody producing cell i.e. a primed B or T lymphocyte. All of the cells of a particular hybridoma cell line express the specific immune potential of the B or T lymphocyte. For example, a B cell hybridoma continuously secretes pure monoclonal antibody of a specificity determined by the immune potential of the parental B cell. Thus, such a cell line may be used for the large scale production of the specific antibodies produced by the B cell. Hybridoma cell lines are permanently adapted to growth in culture, but may also form specific antibody producing tumors in vivo.

The term "immunoconjugate" as used herein, refers to a composition comprising an antibody linked to a second molecule such as a detectable label or effector molecule or "effector moiety". In an exemplary embodiment, the antibody is linked to the second molecule by covalent linkage.

The term "effector moiety" means the portion of an immunoconjugate intended to identify the presence of an immunoconjugate. Thus, in an exemplary embodiment, the effector moiety is, for example, a detectable moiety, e.g., a fluorescent label.

In the context of an immunoconjugate, a "detectable label" or "detectable moiety" refers to a portion of the immunoconjugate which has a property rendering its presence detectable. For example, the immunoconjugate may be labeled with a radioactive isotope which permits cells in which the immunoconjugate is present to be detected in immunohistochemical assays. A "detectable label" or a "detectable moiety" is a composition detectable by spectroscopic, photochemical, biochemical, immunochemical, chemical, or other physical means. For example, useful labels include radioisotopes (e.g., $^3H$, $^{35}S$, $^{32}P$, $^{51}Cr$, or $^{125}I$), fluorescent dyes, electron-dense reagents, enzymes (e.g., alkaline phosphatase, horseradish peroxidase, or others commonly used in an ELISA), biotin, digoxigenin, or haptens and proteins which can be made detectable, e.g., by incorporating a radiolabel into the peptide or used to detect antibodies specifically reactive with the peptide. An introduction to labels, labeling procedures, and detection of labels is found e.g., in Polak and Van Noorden *Introduction to Immunocytochemistry,* 2nd ed., Springer Verlag, NY (1997); and in Haugland *Handbook of Fluorescent Probes and Research Chemicals*, a combined handbook and catalogue Published by Molecular Probes, Inc. (1996).

The term "immunologically reactive conditions" includes reference to conditions which allow an antibody generated to a particular hapten/epitope to bind to that hapten/epitope to a detectably greater degree than, and/or to the substantial exclusion of, binding to substantially all other haptens/epitopes. As is well known in the art, immunologically reactive conditions are dependent upon the format of the antibody binding reaction and typically are those utilized in immunoassay protocols or those conditions encountered in vivo (see Harlow & Lane, ANTIBODIES, A LABORATORY MANUAL, Cold Spring Harbor Press, New York (1988) and Harlow & Lane, USING ANTIBODIES, A LABORATORY MANUAL, Cold Spring Harbor Press, New York (1999), for a description of immunoassay formats and conditions that can be used to determine specific immunoreactivity). In an exemplary embodiment, the immunologically reactive conditions employed are "physiological conditions" which include reference to conditions (e.g., temperature, osmolarity, pH) that are typical inside a living mammal or a mammalian cell. While it is recognized that some organs are subject to extreme, conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The term "binding specificity," "specifically binds to an antibody" or "specifically immunoreactive with," when referring to an epitope, refers to a binding reaction which is determinative of the presence of the epitope in a heterogeneous population of proteins and other biologics. Thus, under designated immunoassay conditions, the specified antibodies bind to a particular hapten at least about two times the background and more typically more than about 10 to about 100 times background. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate (see, e.g. Harlow & Lane, *Using Antibodies, A Laboratory Manual* CSHLP (1999)).

Conservative substitution tables providing functionally similar amino acids are well known in the art. For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The expression "conservatively modified variants" and it equivalents applies to both nucleic acid and amino acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

The terms "identical" or percent "identity," in the context of two or more nucleic acid or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, 95%, 96%, 97%, 98%, or 99% identity over a specified region), when compared and aligned for maximum correspondence over a designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

While any method known in the art for making such determinations may be used, for the purpose of the present invention, the BLAST algorithm, described in Altschul et al., J. Mol. Biol. 215, 403-410, (1990) and Karlin et al., PNAS USA 90:5873-5787 (1993), and incorporated herein by reference, may be used preferentially for determining sequence identity according to the methods of the invention. A particularly useful BLAST program is the WU-BLAST-2 program (Altschul et al., Methods in Enzymology, 266: 460-480 (1996) also incorporated herein by reference). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A percent sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

A polypeptide is also considered to be substantially identical to a second polypeptide, for example, where the two peptides differ only by conservative substitutions. An indication that two nucleic acid sequences are substantially identical is that the two molecules or their complements hybridize to each other under stringent conditions, as described below. Another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The term "substantial identity" or "substantial homology" means that two peptide sequences, when optimally aligned, such as by the programs GAP or BESTFIT using default gap weights, share at least 80 percent sequence identity, preferably 90 percent sequence identity, more preferably at least 95 percent sequence identity or more (e.g., 99 percent sequence identity). Preferably, residue positions which are not identical differ by conservative amino acid substitutions.

The term "substantially pure" "pure", "purified" or "isolated" means an macromolecular species e.g. a particular stable conformation of a macromolecule having at least two stable macromolecule conformations, is the predominant species present (e.g., on a molar basis it is more abundant than any other individual species in the composition). In some exemplary embodiments, a substantially purified fraction is a composition wherein the object species comprises at least about 50 percent (on a molar basis) of all macromolecular species present. Generally, a substantially pure composition will comprise more than about 80 to 90 percent by weight of all macromolecular species present in a composition. Typically, the object species is purified to essential homogeneity (contaminant species cannot be detected in the composition by conventional detection methods) wherein the composition consists essentially of a single macromolecular species e.g., a single macromolecular conformation.

The expression "homogeneous population of purified macromolecules" as used herein refers to a population of macromolecules e.g. a population of prion proteins, the composition of which is homogeneous with respect to type e.g., conformational. For example, prion proteins are known to exist in at least two stable macromolecular conformations but can be purified from one another to provide "homogeneous populations of purified macromolecules" each comprising a homogeneous population of a particular conformer.

The term "homogeneous" or the term "homogeneous population" as used herein typically refers to a population wherein at least about 80% of the molecules comprising the population are of the same type e.g., the same protein as determined by amino acid sequence, or in some exemplary embodiments the same conformational type. In some exemplary embodiments a population is "homogeneous" when at least about 85% of the macromolecules comprising the population are of the same type. In other exemplary embodiments, a population is "homogeneous" when at least about 86%, 87%, 88%, or 89% of the macromolecules comprising the population are of the same type. In still other exemplary embodiments, a population is "homogeneous" when at least about 90%, 91%, 92%, 93%, 94%, 95%, 96%, 97%, 98%, 99%, or 100% of the macromolecules comprising the population are of the same type.

I. Introduction

While the methods of the invention are useful to distinguish among a plurality of protein conformers of the same protein. In an exemplary embodiment protein conformers in a sample comprising a protein having at least two protein conformations are distinguished. The method comprises the steps of: (a) reacting the sample with a protein-modifying reagent which reacts differentially with a first protein conformer and a second protein conformer under conditions whereby the reagent forms one or more covalent bond or bonds with the first protein conformer and either does not form a covalent bond with the second protein conformer or forms a covalent bond or bonds with the second protein conformer that is or are different from the covalent bond or bonds formed with the first protein conformer; (b) treating the reacted sample of step (a) with a protein-cleaving reagent under conditions whereby a peptide bond or bonds in the reacted first protein conformer is cleaved to form at least one unique modified peptide and whereby a peptide bond or bonds in the reacted second protein conformer is cleaved to form a unique different peptide from the unique modified peptide of the first protein conformer; and (c) analyzing the treated sample of step (b) to determine the presence of the unique modified peptide of the first protein conformer or to determine the presence of the unique different peptide of the second conformer.

The invention may also include analyzing the treated sample to determine the presence of both the unique modified peptide of the first protein conformer and the unique different peptide of the second protein conformer. The peptides may be identified by various methods such as: mass spectrometric, colorimetric, immunometric, fluorometric, or radiometric detectors with or without prior chromatographic separation.

A further embodiment comprises quantitating the modified peptide formed by the first protein conformer and may also include quantitating the peptide formed by the second protein conformer.

In the embodiment of the invention wherein the protein comprises more than two protein conformations, the method is carried out as above. Using the methods of the invention, chemical markers can be created that are unique to each conformer of the same protein, and the ratio or absolute amounts of each conformer can be determined.

As noted above, in the methods of the invention, the protein is treated with a protein-modifying reagent which reacts differentially with the different protein conformers. In this aspect, the methods of the invention exploit the difference in susceptibility of one or more amino acid residue(s) within different protein conformations, to a protein-modifying reagent by virtue of its changed spatial location and different chemical reactivity. Some amino acid residues are on the surface of the protein in one conformation and hidden in another. An amino acid residue on the surface of one conformer may be susceptible to covalent modification by protein-modifying reagents, while, on another conformer, the same amino acid residue may be buried within the protein and not be susceptible to the same covalent modification. Thus, the invention is effective to detect if only one conformer of a protein is present in the test sample or to distinguish among two or more conformers of a protein that are present in the test sample.

For purposes of this invention, a protein modifying reagent which reacts differentially includes monofunctional reagents (also denoted as monodentate reagents) and bifunctional reagents.

Monofunctional reagents are chemical reagents that possess only one reactive group and result in the modification of a single amino acid or a single class of amino acid, for example, reaction with the free carboxylic acid moiety in ASP or GLU. An example would be acetyl chloride which converts lysine to its acetylated derivative, (but only if that lysine is on the surface of a protein and not involved in a salt bridge to glutamates or aspartates). Another example of a monofunctional reagent is acetic anhydride which results in a variety of differentially modified protein products as described in detail in Example 2, below.

Bifunctional reagents include (a) homobifunctional crosslinking reagents which are chemical reagents with two identical reactive groups (e.g. acyl halide) connected by a linker of varying length; (b) heterobifunctional crosslinking reagents which are chemical reagents with two different reactive groups connected by a linker of varying length and (c) "zero-length" crosslinking reagents which are chemical reagents that lead to internal crosslinks in proteins and result in loss of mass (e.g. loss of $H_2$ or $H_2O$). Examples of homobifunctional crosslinking reagents are 1) the amino-specific reagent bis(succinimidyl)suberate ($BS^3$) and 2) ethylene glycobis(succinimidylsuccinate) (EGS). Zero-length cross-linking reagents include oxidants that convert two cysteines to one cysteine ($—H_2$) and carbodiimides that link aspartate or glutamate to lysine ($—H_2O$), for example, 1-ethyl-3-(3-dimethylaminopropyl)carbodiimide (EDC). An example of a heterobifunctional crosslinking reagent is N-(alpha-maleimidoacetoxy)-succinimide ester (AMAS) which reacts with both free CYS and amino acids with amino groups (e.g. LYS).

Any of these reagents (monofunctional, homobifunctional or heterobifunctional) may also contain chromophores, fluorophores, radioactive atoms or antibody epitopes to facilitate detection.

Protein-modifying reagents include, but are not limited to, reagents capable of one or more of the following:

Forming a covalent bond with the free α-amino group of the protein conformer.

Forming a covalent bond with the α-amide nitrogen of: Alanine (A), Cysteine (C), Aspartic Acid (D), Glutamic Acid (E), Phenylalanine (F), Glycine (G), Histidine (H), Isoleucine (I), Lysine (K), Leucine (L), Methionine (M), Asparagine (N), Proline (P), Glutamine (Q), Arginine (R), Serine (S), Threonine (T), Valine (V), Tryptophan (W), and/or Tyrosine (Y).

Forming a covalent bond with the hydroxy group of: Serine (S), and/or Threonine (T).

Forming a covalent bond with the phenolic group of: Tyrosine (Y).

Forming a covalent bond with an oxygen of the carboxylate of: Aspartic Acid (D) and/or Glutamic Acid (E).

Forming a covalent bond with the carbon of the carboxylate of: Aspartic Acid (D) and/or Glutamic Acid (E).

Forming a covalent bond with the co-amide nitrogen of: Asparagine (N) and/or Glutamine (Q).

Forming a covalent bond with the one or more of the guanidino nitrogens of Arginine (R).

Forming a covalent bond with the &amine nitrogen of: Lysine (K).

Forming a covalent bond with the aromatic nitrogen of: Histidine (H) or Tryptophan (W).

Forming a covalent bond with the aliphatic carbons of: Alanine (A), Cysteine (C), Aspartic Acid (D), Glutamic Acid (E), Phenylalanine (F), Histidine (H), Isoleucine (I), Lysine (K), Leucine (L), Methionine (M), Asparagine (N), Proline (P), Glutamine (Q), Arginine (R), Serine (S), Threonine (T), Valine (V), Tryptophan (W), and/or Tyrosine (Y).

Forming a covalent bond with the aromatic carbons of: Phenylalanine (F), Histidine (H), Tryptophan (W), and/or Tyrosine (Y).

Forming a covalent bond with the aliphatic α-carbons of: Alanine (A), Cysteine (C), Aspartic Acid (D), Glutamic Acid (E), Phenylalanine (F), Glycine (G), Histidine (H), Isoleucine (I), Lysine (K), Leucine (L), Methionine (M), Asparagine (N), Proline (P), Glutamine (Q), Arginine (R), Serine (S), Threonine (T), Valine (V), Tryptophan (W), and/or Tyrosine (Y).

Forming a covalent bond with the sulfur atoms of: Cysteine (C) and/or Methionine (M).

In addition to the foregoing, the protein-modifying reagent may also be: fluorogenic, chromogenic, biotinylated, immunogenic (reacting with an antibody), covalently bound to a suitable radionucleotide, and/or capable of chelating a rare earth element.

Next, the reacted sample is treated with a protein-cleaving reagent under conditions whereby a peptide bond or bonds in the reacted first protein conformer is cleaved to form at least one unique modified peptide and whereby a peptide bond or bonds in the reacted second protein conformer is cleaved to form a unique different peptide from the unique modified peptide of the first protein conformer. The protein-cleaving reagent can be a chemical agent or a protease.

Chemical agents include, but are not limited to, chemical reagents that cleave amide bonds in proteins such as cyanogen bromide and 2-nitro-5-thiocyanobenzoic acid.

Proteases include: Enzymes capable of cleaving a peptide bond, such as but not limited to proteinase K, trypsin, chymotrypsin; Genetically engineered enzymes that hydrolyze the carboxyl group, in a peptide bond, of the following: Phenylalanine (F), Tryptophan (W), and/or Tyrosine (Y); Genetically engineered enzymes that hydrolyze the carboxyl group, in a peptide bond, of the following: Lysine (K) and/or Arginine (R); Enzymes capable of cleaving a peptide bond that have a strong preference (>10 fold) for cleavage of a specific amino acid at the C or N terminus of the amide bond, such as LYS-C, GLU-C, ARG-C or ASP-N; Enzymes capable of cleaving a peptide bond that have a strong preference (>10 fold) for cleavage of two specific amino acid at the C or N terminus of the amide bond, such as trypsin; Enzymes capable of cleaving a peptide bond that have a strong preference (>10 fold) for cleavage of three specific amino acid at the C or N terminus of the amide bond, such as chymotrypsin; Enzymes capable of cleaving a peptide bond that have a strong preference (>10 fold) for cleavage of four specific amino acid at the C or N terminus of the amide bond; Enzymes capable of cleaving a peptide bond that have a strong preference (>10 fold) for cleavage of five specific amino acid at the C or N terminus of the amide bond; Enzymes capable of cleaving a peptide bond that have a strong preference (>10 fold) for cleavage of six specific amino acid at the C or N terminus of the amide bond.

In cases where the unique peptide(s) contain glycosylation sites, (such as at ASN 181 or ASN 197 in Syrian Hamster PrP), the yield of the unique peptide(s) can be improved by treating the mixture after proteolysis with an enzyme such as PNGase that removes the N-linked oligosaccharides.

Next, the treated sample of step (b) is analyzed to determine the presence of the unique modified peptide of the first protein conformer or determine the presence of the unique different peptide of the second protein conformer. The invention may also include the step of analyzing the treated sample to determine the presence of both unique peptides. The peptides may be identified by various methods such as: mass spectrometric, colorimetric, immunogenic, fluorometric, or radiometric detectors with or without prior chromatographic separation.

Without being limited thereto, analyzing may include using chromatography to separate the peptides and the following methods to identify the peptides: mass spectroscopy; fluorescence; difference in color; difference in ability to bind to streptavidin; difference in the ability to bind to an antibody; difference in the ability to chelate metals.

The methods of the invention are useful for detecting and/or differentiating protein conformers in a sample.

The invention provides a means to detect and/or differentiate prion protein conformers, $PrP^{Sc}$ and $PrP^{C}$. There is considerable pressure to demonstrate the safety of beef and beef products worldwide, and the invention assay to detect low levels of prions in live animals fills an important need.

The invention can also be used for other prion-based or plaque-forming brain diseases.

Samples for use in the assay include, but are not limited to, tissues and biological fluids such as brain, muscle, blood, tonsil, spleen, and lymphatic tissues and cells in cell culture. Furthermore, in-vitro biochemical samples such as preparations of synaptosomes, liposomes, and endoplasmic reticulum vesicles may be used for this protein conformer assay.

II. Immunometric Detection

In an exemplary embodiment, antibodies are used for immunometric detection of and distinguishing between different protein conformers.

As noted earlier, many proteins which exist as populations comprising at least two stable macromolecular conformations are difficult to raise antibodies against. Indeed, the phenomena is particularly well known with respect to prions (see e.g., U.S. Pat. No. 7,259,246 Kascsak et al., (1987) J. Virol (1987) 61, 3688-3693; Prusiner, (1993) Proc. Natl. Acad. Sci. U.S.A. (1993) 90, 10608-10612; and Serban et al., (1990) Neurology (1990) 40, 110-117). Without being bound by theory, it is believed that difficulties in raising monoclonal as well as polyclonal antibodies is the highly conserved amino acid sequence of PrP in mammals which apparently prevents an antibody response against most epitopes.

Fortunately however, the present inventors have now discovered means for making sensitive antibodies to different individual protein conformers.

$PrP^C$ is a normal cellular protein that is expressed in a number of tissues in mammals. A prion ($PrP^{Sc}$) is an infectious protein believed to be the cause of transmissible spongiform encephalopathies. The structures of $PrP^C$ and $PrP^{Sc}$ have been extensively studied. There are no known covalent differences between these proteins. Indeed, they have identical amino acid compositions, identical covalent post-translational modifications (e.g., both have a glycophosphatidylinositol (GPI) anchor, glycosylation, and a single disulfide bond). Thus the sole difference post-translational between $PrP^C$ and $PrP^{Sc}$ is not covalent, instead it is conformational. Thus, $PrP^C$ and $PrP^{Sc}$ are isoforms.

The present inventors have now discovered that the conformational differences between different isoforms of a protein can be exploited to prepare sensitive antibodies that can be used to detect the presence of each of the different conformers.

Conformational differences result in identical amino acids residing in different chemical environments. By residing in a different chemical environments, these amino acids will have different chemical reactivity to identical reagents.

Thus, antibodies to different individual protein conformers can be prepared by first purifying and separating the conformers from one another. Chemical reagents which react differently with each isoform are then used to covalently modify the purified individual conformers and thus, create new immunogenic haptens which distinguish the different conformers and which can be used to raise antibodies to the modified conformers. Antibodies to the modified conformers can in turn be used to immunometrically detect and or distinguish the conformers from one another.

A. Separating and Purifying Individual Protein Conformers

Conformational differences impart physical differences which allow protein conformers to be separated. Any suitable method known in the art can be used for the separation of protein conformers. The skilled artisan will appreciate the physical differences between different isoforms of their protein of interest, and will exploit these differences to separate the isoforms from one another.

1. Separating Conformers of Proteins Having at Least Two Stable Macromolecular Conformations from a Mixture of Proteins and/or Cellular Material Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Alternatively, the molecular weight of a protein of interest having at least two stable macromolecular conformations can be used to isolate the protein of interest from proteins of greater and lesser size, for example, using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

In an exemplary embodiment, conformers of proteins having at least two stable macromolecular conformations can be separated from each other and from other proteins on the basis of size, net surface charge, hydrophobicity, and affinity for ligands. All of these methods are well known in the art. It will be apparent to one of skill that chromatographic techniques can be performed at any scale and using equipment from many different manufacturers (e.g., Pharmacia Biotech).

2. Separating conformers of Proteins Having at Least Two Stable Macromolecular Conformations from One Another In general, conformational differences impart physical differences which allow conformers of proteins having at least two stable macromolecular conformations to be separated from each other. The skilled practitioner appreciates that In an exemplary embodiment, the protein of interest is prion protein. As noted above, prion protein exists in at least two stable conformations or isoforms, $PrP^C$ and $PrP^{Sc}$. $PrP^C$ is a normal cellular protein that is expressed in a number of tissues in mammals. $PrP^C$ is highly conserved in mammals which suggests an import function, however, to date that function remains unclear. $PrP^{Sc}$ is an alternative conformation of prion protein that is infectious and which is believed to be the cause of transmissible spongiform encephalopathies.

Conformational differences between $PrP^C$ and $PrP^{Sc}$ impart physical differences which allow these conformers to be separated. For example, $PrP^{Sc}$ is insoluble in non-denaturing detergents, whereas $PrP^C$ is soluble in non-denaturing detergents. Therefore in an exemplary embodiment, ultracentrifugation in a non-denaturing detergent provides a convenient means of isolating $PrP^{Sc}$ (see e.g., Cohen et al., (1998) Ann. Rev. Biochem 67, 793-819 and U.S. Pat. No. 6,166, 187).

$PrP^C$ is also binds to cation-exchange columns as well as immobilized metal-affinity columns. Thus in exemplary embodiments, these properties are exploited to purify $PrP^C$ and $PrP^{Sc}$ (see e.g., Müller H, et al. (2005) Biochem J. May 15; 388(Pt 1):371-378).

$PrP^{Sc}$ exists in two forms a proteinase K (PK) sensitive and PK resistant form. Without being bound by theory it is believed that these two forms differ in terms of the extent of their oligomerization. The two forms of $PrP^{Sc}$ can be separated by differential ultracentrifugation by methods known in the art see e.g., Pastrana, M. A., et al. (2006) Biochemistry. Volume 45(51); 15710-15717. PK-sensitive PrPSc is completely degraded under standard conditions (50 g/ml of proteinase K at 37° C. for 1 h) and can also be digested with trypsin. Centrifugation in a sucrose gradient reveals that the proteinase K sensitive $PrP^{Sc}$ corresponds to the lower molecular weight fractions of the continuous range of oligomers that comprise $PrP^{Sc}$. PK-sensitive $PrP^{Sc}$ has the ability to convert PrPC into protease-resistant PrPSc, as assessed by the protein misfolding cyclic amplification assay (PMCA) (see e.g., Pastrana, M. A., et al. (2006) supra).

As indicated above, in exemplary embodiments, the invention is applied to characterizing or determining the presence of any protein which assumes two different conformational shapes. In some exemplary embodiments the protein which assumes two different conformational shapes is yeast prion see e.g., Wickner R B, et al (2004). Prions of yeast are genes made of protein: amyloids and enzymes. Cold Spring Harb. Symp. Quant. Biol. 2004; 69:489-96.

In some exemplary embodiments the protein which assumes two different conformational shapes the peanut allergen arh 1. peanut allergen arh 1 is an oligomer of monomers and two distinct conformers can be isolated. Size exclusion chromatography (SEC), ammonium sulfate precipitation (ASP) or hydrophobic interaction chromatography (HIC) can be used to isolate the oligomer of monomers. Anion exchange chromatography (AEC) can be used to isolate a stable trimer see e.g., van Boxtel E L, et al (2006) J. Agric. Food Chem. 54: 7180-7186.

In other exemplary embodiments the different conformational shapes are, like $PrP^{Sc}$, associated with oligomerized and non-oligomerized forms. Typically, one conformation is oligomerized and insoluble, and associated with disease. Some exemplary diseases associated with insoluble proteins which assume two or more different conformations include, but are not limited to: Alzheimer's Disease, Creutzfeld Jakob disease, scrapie and bovine spongeform encephalopathy, ALS, Parkinson's disease, Lewy body, Diabetes Type 1, Senile cardiac and Transthyretin systemic amyloidosis, Chronic inflammation, Serum amyloid A Atherosclerosis, Familial amyloidosis etc.

3. Chemical modification of Purified Conformers

In an exemplary embodiment, the invention provides chemically modified protein conformers. As discussed above. The conformational differences between isoforms of the same protein place identical amino in different chemical environments. By virtue of their residence in different chemical environments, amino acids at identical positions in an amino acid sequence will have different chemical reactivity to identical reagents e.g., through different availability of side chains for reaction. Thus, it is possible to choose a chemical modifier that will form different covalent bonds with each of the isoforms, and which thereby can be used to create new haptens for the production of antibodies.

Typically, each isoform is reacted with the same reagent under identical conditions. The reaction products are analyzed to determine which amino acid residues in each isoform have reacted with the reagent. In an exemplary embodiment, following the modification reaction, the whole protein is used to generate antibodies. In other exemplary embodiments, the reacted protein is first fragmented e.g., via enzymatic trypsin digest, as known in the art, and the modified protein fragments are used to generate antibodies. In some exemplary embodiments, a specific modified amino acid is identified and a synthetic version is chemically synthesized using e.g., the well established methods of making peptides on solid phase (see e.g., R. Bruce Merrifield (1963) Journal of the American Chemical Society 85: 2149).

As noted above both monofunctional and bifunctional reagents are useful covalent modifiers. Typically, chemical modifiers that make unnatural structures are useful for creating immunogenic haptens that illicit a large immune response. Exemplary chemical modifiers are known in the art see e.g, Greg T. Hermanson Bioconjugate Techniques. Academic Press, San Diego, Calif., 1996.

In general, chemical modifiers that are very unlike anything found in biology stimulate the most robust immune response. Exemplary molecules that stimulate a robust immune response include, but are not limited to dinitrobenzene, dinitrobenzoic acid, and derivatives thereof.

In one exemplary embodiment, the covalent modifier is 1-fluoro-2,4-dinitrobenzene (FDNB). Under reaction conditions favoring native protein structure FDNB specially reacts with terminal amino moieties on lysine residues that are not sterically hindered by protein folding. The product of the reaction is a modified protein, bearing at least one 2,4-dinitrobenzene (DNB) moiety. DNB-lysine is chemically very unlike anything found in biology. Thus, it is highly immunogenic as a hapten.

The skilled artisan will appreciate that in general, chemical modifications useful for distinguishing between protein conformers are typically directed to that region of the protein that participates in the conformational change or which is known to be affected by conformational differences. However, any chemical modification that is useful for the production of haptens and thus "newly created epitopes" which allow one of skill in the art to raise antibodies that specifically bind to one chemically modified conformer but not the other(s), is suitable for use in the methods disclosed herein.

In an exemplary embodiment, the protein having at least two stable macromolecular conformations is prion protein, PrP. Transgenic rodent experiments have revealed the a subset of the amino acids present in $PrP^{C}$ are typically involved in the conformational changes in PrPC that lead to a prion, PrPSc (see e.g., Fischer M, Rulicke T, Raeber A, Sailer A, Moser M, Oesch B, Brandner S, Aguzzi A, Weissmann C. (1996) Prion protein (PrP) with amino-proximal deletions restoring susceptibility of PrP knockout mice to scrapie. EMBO J. 15, 1255-1264. Flechsig E, Shmerling D, Hegyi I, Raeber A J, Fischer M, Cozzio A, von Mering C, Aguzzi A, Weissmann C. (2000) Prion protein devoid of the octapeptide repeat region restores susceptibility to scrapie in PrP knockout mice. Neuron. 27, 399-408. Weissmann C, Flechsig E. (2003) PrP knock-out and PrP transgenic mice in prion research. Br. Med. Bull. 66, 43-60. Supattapone S, Muramoto T, Legname G, Mehlhorn I, Cohen F E, DeArmond S J, Prusiner S B, Scott M R. (2001) Identification of two prion protein regions that modify scrapie incubation time. J. Virol. 75, 1408-1413. Supattapone S, Bouzamondo E, Ball H L, Wille H, Nguyen H O, Cohen F E, DeArmond S J, Prusiner S B, Scott M. (2001) Mol. Cell. Biol. 21, 2608-2616). This "prion region" is comprises of 53 amino acids including alanine, proline, glycine, leucine, isoleucine, valine, phenylalanine, methionine, glutamine, serine, threonine, tyrosine, lysine, histidine, arginine, and asparagine. These amino acids are likely to be contained in different chemical environment in the different isoforms of prion protein, and as such are good candidates for chemical modification to create a newly created epitope.

Thus, in an exemplary embodiment, the protein having at least two stable macromolecular conformations is prion protein, PrP and a primary amine e.g., the primary amine of lysine, is chemically modified to provide a "newly created antigen". In an exemplary embodiment, primary amines are reacted with a chemical modifier comprising an immunogenic molecule e.g. dinitrobenzene, coupled to a carboxylic acid, a carboxylic acid activated by N-hydroxysuccinimide (NHS), and/or a carboxylic acid activated by a derivative of NHS e.g., a sulfated NHS e.g., N-hydroxysulfosuccinimide, or an NHS comprising a quaternary amine.

In other exemplary embodiments, the primary amine present in lysine reacts with a number of activated esters to produce a novel immunogen covalently attached by a amide bond. Thus in exemplary embodiments, the primary amine present in lysine reacts with N-hydroxysuccinimide (NHS) esters of any organic carboxylic acid. Exemplary N-hydroxysuccinimide (NHS) esters of organic carboxylic acids include, but are not limited to N-hydroxysulfosuccinimide (Sulfo-NHS) activated esters and other ionic variants of NHS that increase the solubility of the activated ester. In some exemplary embodiments the activated NHS ester is generated in situ by using a water soluble coupling agent, 1-ethyl-3-(3-dimethylaminopropyl) carbodiimide hydrochloride (EDC), a water soluble activated NHS or NHS derivative, and a carboxylic acid.

In other exemplary embodiments, the primary amine present in lysine reacts with isothiocyanates to produce a novel immunogen covalently attached by an isothiourea bond. In this embodiment an immunogenic molecule is bound to an isothiocyanate functionality and it is allowed to react with the primary amine of lysine.

In still other exemplary embodiments, the primary amine present in lysine reacts with sulfonyl chloride to produce a novel immunogen covalently attached by an sulfonamide bond. In this embodiment an immunogenic molecule is bound to a sulfonyl chloride functionality and it is allowed to react with the primary amine of lysine.

In still other exemplary embodiments, the primary amine present in lysine reacts with acyl azides to produce a novel immunogen covalently attached by an amide bond. In this embodiment an immunogenic molecule an immunogen is bound to an isothiocyanate functionality and it is allowed to react with the primary amine of lysine.

In still other exemplary embodiments, the primary amine present in lysine reacts with aldehydes to produce a novel immunogen covalently attached by a Schiff's base. In some exemplary embodiments, the Schiff's base is reduced to the corresponding secondary amine by reducing agents such as sodium cyanoborohydride (NaCNBH3). In this embodiment an immunogenic molecule is bound to an aldehyde functionality and it is allowed to react with the primary amine of lysine and then reduced.

In still other exemplary embodiments, the primary amine present in lysine reacts with epoxide derivatives to produce a novel immunogen covalently attached by a secondary amine bond. In this embodiment an immunogenic molecule is bound to an epoxide functionality and it is allowed to react with the primary amine of lysine to produce a secondary amine.

In still other exemplary embodiments, the primary amine present in lysine reacts with aryl halides, e.g., fluororbenzene or 2,4-dinitrofluorobenzene to produce a novel immunogen covalently attached by an arylamine bond. In this embodiment an immunogenic molecule is bound to an arylhalide functionality and it is allowed to react with the primary amine of lysine to produce the immunogenic arylamine.

In still other exemplary embodiments, the primary amine present in lysine reacts with imidoester compounds to produce a novel immunogen covalently attached by an amidine bond. In this embodiment an immunogenic molecule is bound to an imidoester functionality and it is allowed to react with the primary amine of lysine to produce an amidine bond.

In other exemplary embodiments, the hydroxy functional groups of serine and threonine are activated by reagents such as N,N'-carbonyl dimidazone (CDI) or N,N'-carbonyl disuccinimidyl carbonate (DSC) to yield the corresponding imidazolyl carbamate or succinimidyl carbamate which can be reacted with a suitable primary amine to yield the corresponding carbamate. In an exemplary embodiment, the reaction yields an immunogenic carbamate.

In other exemplary embodiments, the hydroxy functional groups of serine and threonine can converted to a carbamate by reaction with an isocyanate compound. This reaction would yield an immunogenic carbamate.

In other exemplary embodiments, the tyrosine and histadine, which possess an aromatic functionality, are modified by iodine. Iodide in the presence of an oxidizing agent, e.g., chlorine, produce an activated form of iodine that can produce iodinated histidine or tyrosine residues, which are immunogenic.

Having chosen a suitable chemical modifier, reaction conditions are chosen which ensure modification of the protein conformer(s). In an exemplary embodiment, reactions involving a primary amine take place in buffers that do not have a nucleophilic nitrogen e.g., MOPS typically at pH 6.5-7.9; MES typically at pH 5.5-6.7, Phosphate at pH 3-9 etc.

Buffers comprising nucloephilic nitrogens include, but are not limited to TRIS based buffers, and buffers comprising ethylamine, methylamine, ammonium carbonate, ammonium acetate, etc.

As is appreciated by one of skill in the art, other proteins that exist in at least two stable macromolecular conformations e.g., amyloid—beta protein see e.g., McLean C A, et al (1999) Ann Neurol. 1999; 46: 860-866 and yeast prion see e.g., Kushnirov V V, et al. (2006). Purification and analysis of prion and amyloid aggregates. Methods. 2006; 39: 50-5) can be analyzed in a manner analogous to that described above for prion protein, to determine the relative likelihood that a particular amino acids may be part of a sequence that is likely to be in a different chemical environment.

Chemically modified proteins, or protein fragments, are purified and used for the generation of antibodies.

4. Preparation of Antibodies to the Chemically Modified Protein Conformers or Chemically Modified Protein Conformer Fragments Methods of producing polyclonal and monoclonal antibodies that react specifically with an chemically modified protein conformers or chemically modified protein conformer fragments are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., Science 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-chemically modified protein conformers or non-chemically modified protein conformer fragments, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a chemically modified protein conformer domain, can also be made, by subtracting out antibodies directed against other parts of the protein.

Once the specific antibodies against the chemically modified protein conformers or chemically modified protein conformer fragments are available, the antibodies can be sequenced, or can be manipulated so as create chimeric antibodies. Alternatively, chemically modified protein conformers or chemically modified protein conformer fragment specific antibodies of the invention may be used to detect chemically modified protein conformers by a variety of immunoassay methods. For a review of immunological and immunoassay procedures, see Basic and Clinical Immunology (Stites & Terr eds., $7^{th}$ ed. 1991).

5. Characterization of Monoclonal Antibodies a. Isotype Determination

Mammalian immunoglobins have been classified into five primary classes (IgG, IgM, IgA, IgD and IgE) according to differences in their heavy chain polypeptides. Several of these classes can be further divided into subclasses, e.g., $IgG_1$, $IgG_2$, $IgG_3$, $IgG_4$, $IgA_1$, and $IgA_2$. These classes can be identified based on their reaction to antisera. Similarly, mammalian light chain constant regions can be assigned to one of two clearly distinct isotypes based on their amino acid sequence and reactions to different antisera. These isotypes are called κ (kappa) and λ (lambda).

Because the biological functions and biochemical characteristics of classes and isotypes differ, distinguishing the classes and isotypes of an immunoglobulin molecule is critical. Although any immunoaffinity method method known in the art for can be used to determine antibody isotypes. The following provides an example of isotyping using an ELISA to determine the isotype of mouse antibodies.

For the ELISA assay, anti-mouse immunoglobulin antibodies are coated onto each well of a 96-well microtiter plate that serves as a solid support. Sample mouse immunoglobulins in solution are added and captured by the anti-mouse antibodies. Specific anti-mouse isotyping antibodies are then introduced and allowed to bind to the mouse-anti-mouse antibody complex. Finally, an enzyme-tagged antibody that reacts specifically with the anti-isotyping antibodies is added, which, together with a colorimetric substrate, indicate the immunoglobulin isotype of the sample. Antibody isotyping is well known in the art and kits are commercially available (e.g., isotyping kits such as the Isodetect kit are available from Stratagene, La Jolla, Calif.).

B. Epitope Mapping and Competitive Binding Assay

Regions of a given polypeptide that include an epitope can be identified using any number of epitope mapping techniques known in the art (see e.g., Epitope Mapping Protocols in Methods in Molecular Biology, Vol. 66 (Glenn E. Morris, ed., 1996) Humana Press, Totowa, N. J.) Methods for epitope mapping may include solving the crystal structure of an antibody-antigen complex or may involve analysis of vast libraries of random peptide sequences. However, the most convenient methods typically involve synthetic peptide based assays and competition assays.

Linear epitopes may be determined by synthesizing large numbers of peptides corresponding to portions of a protein molecule such as chemically modified protein conformers on solid supports, and then reacting the peptides with antibodies while the peptides are attached to the supports. In this method, a set of overlapping peptides is synthesized, each corresponding to a small linear sequence of the antigen and arrayed on a solid phase. The panel of solid phase peptides is then probed with test antibodies and bound antibody is detected using enzyme-labeled secondary antibody. Methods for mapping linear epitopes are known in the art (see, e.g., Harlow and Lane, supra).

Alternatively, antigenic epitopes can be mapped by competition assay. Competition assay is a widely used method for determining if two antibodies are able to bind independently to the same protein antigen or whether their binding sites on the same protein overlap in such a way that both are not able to bind to the antigen at the same time.

Any method known for conducting a competition assay may be used to determine if a monoclonal antibody binds the same epitope as a particular chemically modified protein conformers antibodies of the invention. For example, an ELISA format may be used. In ELISA the competition assay is initiated by first immobilizing the antigen (e.g., chemically modified protein conformer or fragment thereof) on a solid substrate such as a 96 well plate. All antibodies to be used in the competition assay are then tested in direct binding assays to make certain that they are capable of binding the immobilized antigen. Direct binding assays are known in the art (see e.g., Harlow and Lane, supra). Those antibodies that bind the immobilized antigen in a direct binding assay can be used in the competition assay.

The competition assay is carried out wherein either the characterized antibody or the test antibodies are labeled. In one aspect a label may permit a colorometric enzyme reaction to take place to reveal the presence of the labeled antibody. However, any convenient label may be used. If a colorometric assay is used, the label may be either indirectly or directly attached to the antibody. For example, an indirect label may be a biotin label that subsequently can be bound with a streptavadin peroxidase conjugate to reveal the presence of the antibody. Alternatively, the labeled antibody could be directly labeled with the peroxidase, or the antibody could be bound by a secondary antibody to which an enzyme is conjugated.

In one method of performing an ELISA based competition assay, the characterized antibody is left unlabeled. The characterized antibody is bound in the first step to the immobilized antigen. After the unlabeled characterized antibody has had sufficient time to bind the immobilized antigen, labeled test antibodies are added to the solution and allowed to compete for antigen binding in the presence of the unlabeled characterized antibody. After the test antibody has been given sufficient time to bind to the immobilized antigen (if it can do so), the wells containing the antibodies and antigen are washed to remove all the unbound antibodies, and signal from the label is measured.

If signal from the label is detected in the well after the wash step, then the test antibody binds a different epitope than the unlabeled characterized antibody. Alternatively, if no signal is detected, then the labeled test antibody binds the same epitope as the unlabeled characterized antibody. Similarly, the competition assay may be carried out with an unlabeled test antibody and a labeled characterized antibody. Competition assays are known in the art (see e.g., Harlow and Lane, supra).

c. Labeled Antibodies

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3$H, $^{125}$I, $^{35}$S, $^{14}$C or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The procedure for attaching an effector molecule to an antibody will vary according to the chemical structure of the moiety to be attached to the antibody. Polypeptides typically contain a variety of functional groups; e.g., carboxylic acid (COOH), free amine (—NH2) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules such as those available from Pierce Chemical Company, Rockford Ill.

The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

6. Detecting Antibody-Antigen Complex in a Sample a. Immunoassays

Once produced, the chemically modified protein conformer antibodies may be used in virtually any assay format that employs antibodies to detect antigens. Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules, as discussed in detail above. Assays which amplify the signals from the immune complex are also known; examples of which are assays which utilize biotin and avidin, and enzyme-labeled and mediated immunoassays, such as ELISA assays.

1. ELISA

A chemically modified protein conformer may be used as an antigen in immunoassays such as enzyme-linked immunosorbent assays (ELISA), or in any antibody binding assays or procedures known in the art for the detection of anti-chemically modified protein conformer antibodies. Conversely, the chemically modified protein conformer antibodies of the invention are useful for the detection of chemically modified protein conformers in biological fluids using any number of immunological assay methods known in the art, including ELISA (see, e.g. Ausubel et al. supra).

In ELISA assays, the biological fluid to be tested for the presence of a chemically modified protein conformer is immobilized onto a selected surface, for example, a surface capable of binding proteins, such as the wells of a polystyrene microtiter plate. The solid support is reacted with the chemically modified protein conformer antigen, under suitable binding conditions such that the molecules are sufficiently immobilized to the support. Sometimes, immobilization to the support can be enhanced by first coupling the antigen and/or antibody to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) Bioconjugate Chem. 3:2-13; Hashida et al. (1984) J. Appl. Biochem. 6:56-63; and Anjaneyulu and Staros (1987) International J. of Peptide and Protein Res. 30:117-124.

After washing to remove incompletely adsorbed antigens, a nonspecific protein such as a solution of bovine serum albumin (BSA) that is known to be antigenically neutral with respect to the test sample may be bound to the selected surface. This allows for blocking of nonspecific adsorption sites on the immobilizing surface and thus reduces the background caused by nonspecific bindings of antisera onto the surface.

The immobilizing surface is then contacted with anti-chemically modified protein conformer antibodies of the invention, in a manner conducive to immune complex (antigen/antibody) formation. The mixture is then allowed to incubate for from 2 to 24 hours, at temperatures such as of the order of about 25° C. to 37° C. Following incubation, the anti-chemically modified protein conformer antibody-contacted surface is washed to remove non-immunocomplexed material. The washing procedure may include washing with a solution, such as PBS/Tween or a borate buffer.

Following formation of specific immunocomplexes between the anti-chemically modified protein conformer antibody and the affixed test sample, and subsequent washing, the occurrence, and even amount, of immunocomplex formation may be determined by subjecting the immunocomplex to a second antibody having specificity for the anti-chemically modified protein conformer antibody, as is known in the art. To provide detecting means, the second antibody may have an associated activity such as an enzymatic activity that will generate, for example, a color development upon incubating with an appropriate chromogenic substrate. Quantification may then be achieved by measuring the degree of color generation using, for example, a spectrophotometer.

b. Immunoaffinitycapillary Electrophoresis (ICE)

Capillary electrophoresis (CE) is a separation technique based on the differential migration of charged particles in an electric field (see e.g. Ausubel et al. supra). Basically, the method involves filling a thin capillary (20-100 µm internal diameter) with an electrolyte that provides a medium in which analytes can migrate through. A sample is introduced at one end of the CE unit. An electric field, typically of 100-400 µA constant current, is applied across the capillary to facilitate analyte species migration according to their electrophoretic mobility. The analyte species pass a detector as they migrate (usually UV or fluorescence) at or near the end of the capillary.

Capillary electrophoresis can be adapted to function in combination with immunoaffinity separation techniques to provide a sensitive method for obtaining reliable and reproducible analytical results for extremely small biological samples. Immunocapillary electrophoresis, which may also be known as immunoaffinity capillary electrophoresis or ICE, is aessentially a modified immunoaffinity method that uses an electric field for elution of an antigen from an immunoaffinity column.

In an exemplary embodiment, an anti-chemically modified protein conformer antibody of the invention is immobilized to the internal wall of the first 5-cm of a 100-cm fused silica capillary. There are a large number of methods for covalently attaching antibodies to a solid phase. For example, depending on the isotype, antibodies can be coupled to protein A or protein G beads. Alternatively, antibodies can be coupled to beads that have been chemically modified to have active groups that will covalently bind the antibody. In a preferred embodiment FAb fragments are directly attached via their free thiol groups to thiol groups derivatized directly into the surface chemistry of the internal walls of the capillary as described in T. M. Phillips and P. Smith (2003) Biomed. Chromatogr. 17(2-3):182-187, and in T. M. Phillips (2001) J Biochem Biophys Methods. October 30; 49(1-3):253-62 each of which is herein incorporated by reference.

Samples of biological fluid for of testing are labeled with a dye that can be detected by the detection system, for example a red laser dye that can be detected using laser-induced fluorescence which is known in the art. After the sample is labeled, an aliquot of the labeled biological fluid is introduced into the capillary by vacuum injection. The labeled biological fluid is allowed direct contact with the immobilized antibody coating for at least 10 minutes to ensure that any chemically modified protein conformer antigen is bound by the immobilized anti-chemically modified protein conformer antibody.

Following incubation to bind the chemically modified protein conformer antigen to the immobilized antibody, non-bound material is purged by the application of a neutral pH phosphate buffer wash. The bound material is then recovered by electro-elution at 100-µA constant current with on-line laser-induced fluorescence detection.

7. Assay

In an exemplary embodiment, the invention provides an assay for detecting one or more distinct of a protein having at least two stable macromolecular conformations. The assay comprises providing a sample suspected of containing a protein which assumes a first conformation and a second conformation (e.g., a disease related conformation) and is capable of detecting a disease conformation of the protein when present in a very low concentration relative to the concentration of other proteins and compounds including the non-disease conformation.

EXAMPLES

The following examples are intended only to further illustrate the invention and are not intended to limit the scope of the invention which is defined by the claims.

Example 1

The following example describes differentiation of the two prion conformers, $PrP^C$ and $PrP^{Sc}$ in accordance with the methods of the invention, and wherein a bifunctional reagent is used.

Materials and Methods

Reagents

The water-soluble, amino group selective bifunctional cross-linking reagent bis(succinimidyl)suberate ($BS^3$), was purchased from Pierce (Rockford, Ill.). α-Cyano-4-hydroxycinnamic acid (α-CHC) was purchased from Bruker Daltonics (Billerica, Mass.). Achromobacter lysyl endopeptidase (lys C) was obtained from Wako (Osaka, Japan). Trypsin (sequencing grade, modified) was purchased from Promega (Madison, Wis.). An N-Glycosidase F (PNGase F) deglycosylation kit was obtained from New England Biolabs (Beverly, Mass.). All other reagents were from SIGMA-ALDRICH®.

Syrian Hamster PrP27-30

PrP 27-30 was isolated as described (Diringer et al. (1997)) from brains of terminally ill Syrian hamsters infected with the 263K strain of scrapie. Its purity and approximate concentration was assessed by SDS-PAGE and Coomassie blue staining. PrP 27-30 was suspended immediately before use in 1% sarkosyl at an approximate concentration of 0.2 µg/µl by sonication with a 4710 Series probe ultrasonics homogenizer (Cole Parmer, Chicago, Ill.).

Cross-Linking Reactions

PrP 27-30, ~2-10 µg, was cross-linked in 100 mM phosphate buffer, pH=7.2, at a concentration of 0.067 µg/µl; $BS^3$ was added from a freshly prepared 10 mM stock solution in 5 mM sodium acetate, pH=5, to a final concentration of 1.7 mM, and allowed to react with the protein for 30 minutes at room temperature. The reaction was then terminated by addition of 1M lysine, pH=7.2 to a final concentration of 140 mM and further incubation at room temperature for 15 minutes. Control samples were treated in the same way, except that 5 mM sodium acetate solution, pH=5 was added instead of $BS^3$ solution.

Deglycosylation and Electrophoretic Separation

Cross-linked or control protein was precipitated by centrifugation at 14000 rpm in a table-top centrifuge for 45 minutes; supernatants were carefully aspirated and discarded, and the pellets were rinsed with 200 µl of 85% methanol. Pellets were then denatured and deglycosylated with 3 µl of PNGase solution at 37° C. for 1 hour, according to the manufacturer's instructions. Reaction mixtures were then diluted with an equal volume of reducing Laemmli sample buffer, boiled in 10 minutes and subjected to SDS-PAGE (Laemmli (1970) *Nature* 227:680-685) using 12% gels. Protein bands were stained with Coomassie blue.

In-Gel Proteolytic Digestion

For samples analyzed by MALDI-TOF, protein bands were carefully excised with a razor blade, and then reduced, alkylated and digested in-gel with lys C at an approximate mass ratio of 1:10 trypsin or lysC to PrP, according to the procedure of Shevchenko et al. (Shevchenko et al. (1996) *Anal. Chem.* 68(5):850-858) with slight modifications. Briefly, bands were cut to 1 mm$^3$ pieces, placed in an eppendorf tube, washed with water and dehydrated with 200 µl acetonitrile for 15 minutes using mild agitation. Acetonitrile was removed and the gel pieces were dried in vacuo (SpeedVac, Savant, Farmingdale Calif.); a volume of 30 µl of 10 mM DTT in 25 mM NH$_4$HCO$_3$ was added and the reduction was carried out at 56° C. for 30 minutes. The solvent was then removed, and after dehydration of gel pieces with acetonitrile as described, replaced with 30 µl of 55 mM iodoacetamide. Alkylation was carried on in the dark at RT for 20 minutes. The solvent was then removed and gel pieces were washed with 25 mM NH$_4$HCO$_3$, dehydrated with acetonitrile and rehydrated on ice by addition of 20 µl of 25 mM NH$_4$HCO$_3$ containing 15 ng/µl trypsin or lysC. After 40 minutes, 30 µl of 25 mM NH$_4$HCO$_3$ were added to cover the gel pieces and samples were incubated overnight at 37° C. Digested samples were briefly centrifuged and the supernatant collected. Gel pieces were then extracted with 20 µl of 25 mM NH$_4$HCO$_3$ with sonication for 10 minutes. The solvent was then recovered and replaced with 20 µl of 0.1% trifluoroacetic acid (TFA). The extracts and the digestion solution were pooled and dried in vacuo. Peptides were redissolved in 10 µl of 0.1% TFA, 50% acetonitrile.

For samples analyzed by nanoLC-MS-MS, protein spots were excised from gels then processed in a DigestPro (INTAVIS Bioanalytical Instruments AG, Bergish Gladbach, Germany). Following washing, reduction with DTT, alkylation with iodoacetamide, and in-gel digestion (porcine trypsin, Princeton Separations, Adelphia N.J.), the peptides were eluted into a 96 well collection plate with 60 ul of 10% formic acid containing 0.1% trifluoroacetic acid.

MALDI

A 2 µl portion of protein digest was mixed with an equal volume of a saturated solution of α-CHC in acetonitrile/0.1% aqueous TFA (1/2). One µl of the mixture was spotted on a Bruker sample plate, allowed to air-dry and analyzed using a Bruker Autoflex MALDI instrument in reflectron mode. The laser frequency was 5 Hz. About 30 laser shots were averaged.

Nanospray LC/MS/MS

NanoLC-ESI-MS-MS was done with an Applied Biosystems (ABI/MDS Sciex, Toronto, Canada) Model QStar Pulsar equipped with a Proxeon Biosystems (Odense, Denmark) nano-electrospray source. In-gel digest (20 µl) was loaded automatically onto a C-18 trap cartridge and chromatographed on a reversed-phase column (Vydac 238EV5.07515, 75µ×150 mm; Hesperia, Calif.) fitted at the effluent end with a coated spray tip (FS360-50-5-CE, New Objective Inc., Woburn, Mass.). An LC Packings nano-flow LC system (Dionex, Sunnyvale, Calif.) with autosampler, column switching device, loading pump, and nano-flow solvent delivery system was used to elute the column. Elution solvents were: A (0.5% acetic acid in water) and B (80% acetonitrile, 0.5% acetic acid). Samples were eluted at 250 nl/min with the following gradient profile: 2% B at 0 min to 80% B in a 15 min linear gradient; held at 80% B for 5 min then back to 2% B for 10 min. The QStar Pulsar was externally calibrated daily and operated above a resolution of 10,000. The acquisition cycle time of 6 s consisted of a single is MS "survey" scan followed by a 5 s MS/MS scan. Ions between m/z 400 to 1,000 of charge states between +2 to +5 having intensities greater than 40 counts in the survey scan were selected for fragmentation. The dynamic exclusion window was set to always exclude previously fragmented masses. Collision energy optimized for charge state and m/z was automatically selected by the Analyst QS software after adjusting parameters to obtain satisfactory fragmentation of GLU fibrinogen peptide (+2), and ACTH (+3 and +4). Nitrogen was used for the collision gas and the pressure in the collision cell ranged from 3×10-6 to 6×10-6 torr.

Data Analysis

LC-MS-MS data was internally calibrated using trypsin autolysis peptides whose identity was confirmed by MS-MS. The MSMS data was submitted to Mascot (Matrix Science) to assist in assignment of unmodified peptides present in the digest. (For these peptides an RMS mass error of 10-15 ppm was observed.) Next, the calibrated TOF-MS survey scans were processed with the "LCMS Reconstruct" tool in the Analyst software. The output is a list of peptide molecular weights calculated by deconvolution of multiple charge states and then identification of the monoisotopic $^{12}$C species. Lists of peaks present in spectra of monomeric and dimeric cross-linked samples were compiled. Using custom software written in-house, those peaks also present in spectra of control digests of PrP 27-30 were deleted from cross-linked sample peak lists using a 20 ppm mass tolerance. The resulting experimental list of monoisotopic molecular weights was compared to a list of theoretical cross-linked and modified peptides predicted from the sequence of ShaPrP(90-231) using the X-link search tool of GPMaw (http://welcome.to/gpmaw). For MALDI analysis, peaks were externally calibrated using a peptide mix standard (Angiotensin II, Angiotensin I, Substance P, Bombesin, ACTH clip 1-17, ACTH clip 18-39, Somatostatin 28, Bruker); identified major tryptic fragments predicted from the sequence of ShaPrP(90-231) were then used to internally calibrate unknown peaks.

Results

Treatment of PrP 27-30 with BS$^3$ resulted in cross-linked products, documented by the appearance of new bands on polyacrylamide gels corresponding to dimers, trimers and higher order multimers of PrP 27-30 (FIG. 1). Dimers and trimers were also generated at lower concentrations of BS$^3$ (0.17 mM) although oligomer bands were of lower abundance (data not shown). Cross-linking did not interfere with the ability of PNGase F to completely remove carbohydrate chains (FIG. 1). A control experiment in which the order of addition of the cross-linking and quenching reagent was reversed underwent no cross-linking (data not shown). This control ruled out the possibility that the cross-linked species originated artifactually from residual BS$^3$ during sample manipulation subsequent to the cross-linking reaction, i.e. after the native PrP$^{Sc}$ conformation has been lost. Separate control experiments used recombinant Syrian hamster PrP (residues 90-231) at the same reagent and protein concentrations as done with isolated PrP 27-30. Using the same reaction times and temperatures, or changing these variables to potentially increase yields of reacted products resulted in no dimer band as seen by SDS-PAGE in any of the control reactions (data not shown). These control experiments prove that the dimers formed with PrP 27-30, and the crosslinked peptides resulting from these dimers, are formed exclusively from PrP$^{Sc}$ and are not formed from PrP$^C$.

Figure 2A:
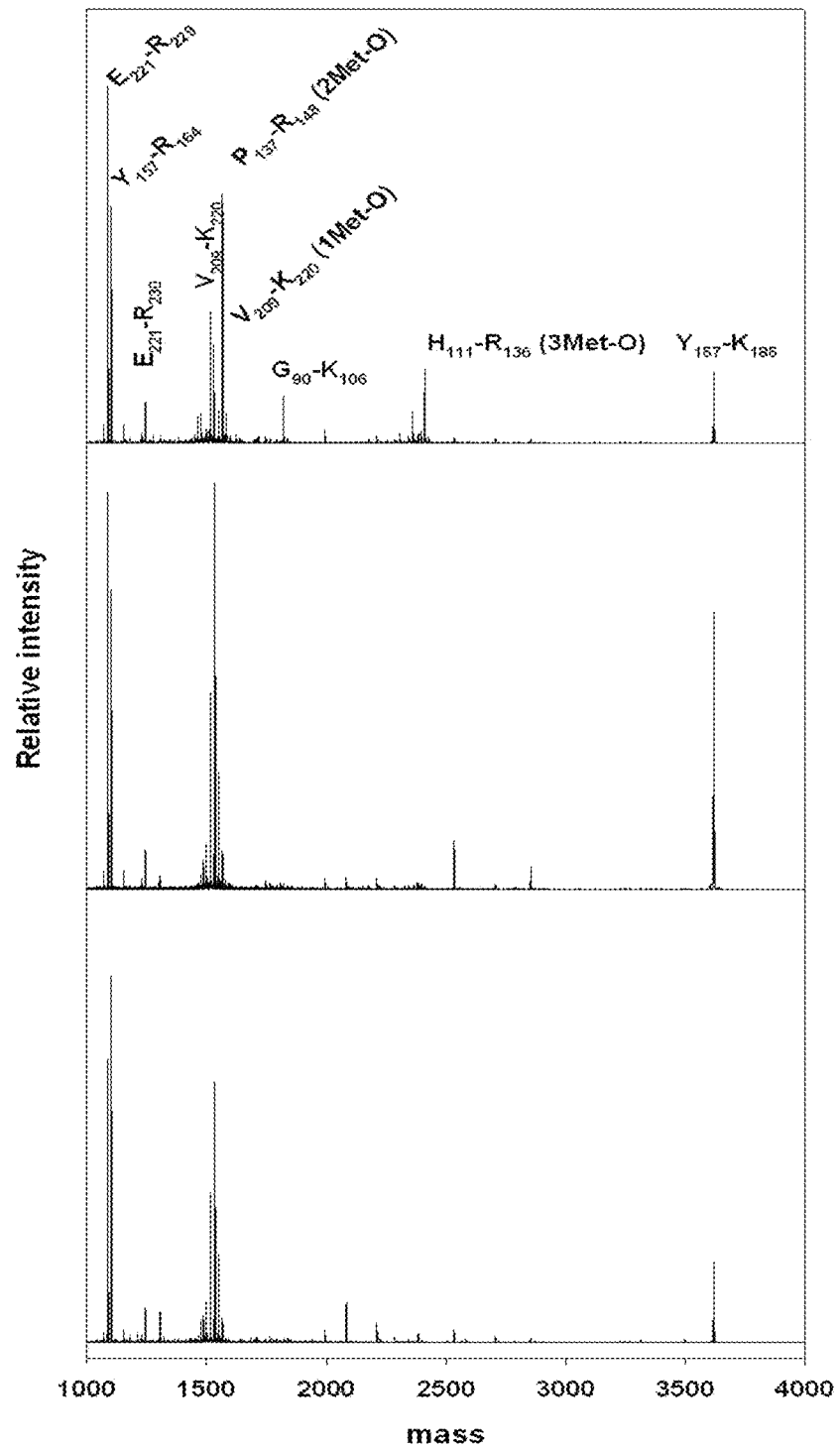
FIG. 2 shows mass spectra of cross-linked monomer and dimer and of control deglycosylated PrP27-30. Bands were excised from gels and digested in gel with trypsin overnight at 37° C. Peptides were extracted, dried in vacuo and analyzed by matrix assisted laser desorption ionization-time of flight (MALDI-TOF) as described. (A) Spectra of control, monomer and dimer digests. The main identified peaks are indicated. For a more comprehensive list of peaks see Table 2. (B) Expanded area showing decrease of the $G_{90}$-$K_{106}$ aminoterminal peptide.

Tryptic digests of PrP 27-30, cross-linked monomer and dimer bands from SDS-PAGE were analyzed by MALDI-TOF (FIG. 2) and nanoLC-ESI-Q-TOF mass spectrometry. Spectra from the cross-linked monomer and dimer bands are very similar to those of control digests of PrP 27-30. Some degree of variability was observed in the relative intensities of some peaks, as a consequence of variable oxidation of peptides containing methionine residues. Also, some variability in cleavage by trypsin at PK positions was observed. Good sequence coverage (88%) of the expected tryptic peptides (Table 1) was observed in all samples and by both techniques. Amino acid residues shown in bold are those which are potential tryptic cleavage sites. The ESI data are summarized in Table 2. RMS mass error for the peptides listed was 12 ppm, and the identity of the indicated sequences was confirmed by MS-MS (data not shown).

TABLE 1

Partial Amino Acid Sequence of Shaprp

86
.......GGGWGQGGGTHNQWNKPSKPKTNMKHMAGAAAAGAVVGGLGGYM

LGSAMSRPMMHFGNDWEDRYYRENMNRYPNQVYYRPVDQYNNQNNFVHDCV

NITIKQHTVTTTTKGENFTETDIKIMERVVEQMCTTQYQKESQAYYDGRRS
231 other amino termini of low abundance. RMS mass error for the 19 peptides found by ESI was 12 ppm, and the identity of the indicated sequences was confirmed by MS-MS (data not shown). The MALDI results are quite similar. Four abundant amino termini were seen (GLY 82, GLY 86, GLY 90 and GLY 92). ESI data shows the amino terminus at GLY 86 to be most abundant, whereas GLY 90 was found to be most abundant by MALDI.

Figure 2B:
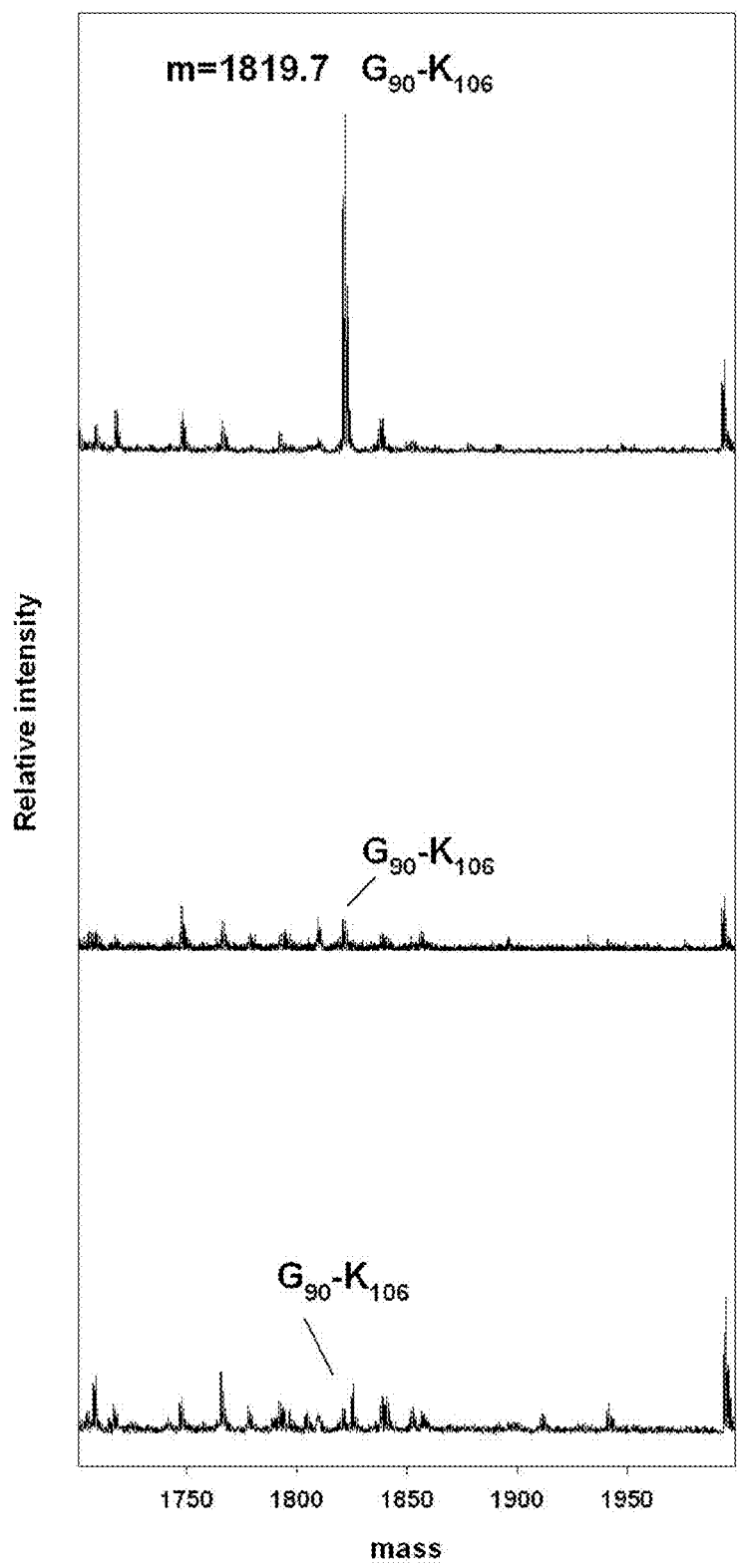

Comparison of the relative abundances of the amino terminal peptides found in the cross-linked monomer and dimer bands to the amounts seen in PrP 27-30 reveals a very marked, consistent decrease in abundance of all the abundant amino terminal species in the cross-linked samples (FIG. 2B and Table 2). This effect was common to spectra of both trypsin and lysC digests (data not shown). While neither ionization method can yield quantitative data without use of isotopically-labeled standards, these results strongly suggest that amino terminal amino groups extensively react with BS$^3$. The decreased abundances of the amino terminal species in the cross-linked samples is also indicative of exposed locations of the various amino termini allowing facile reaction with the large and ionic crosslinking reagent.

Direct evidence of reaction of the amino termini with BS$^3$ was also observed (Table 3). Four tryptic peptides were found as their suberic acid amides (M+C$_8$H$_{12}$O$_3$), formed by reaction of BS$^3$ with the amino terminus of the peptide followed by hydrolysis of the remaining N-hydroxysuccinimide ester. The modified peptides were assigned to residues 82-106, 86-106, 90-106 and 92-110 which correspond to four of the more abundant amino-terminally truncated PrP 27-30 species (see FIG. 3). RMS mass error for the six measurements (three from the dimer band and three from the monomer band from

TABLE 2

| | Electrospray Ionization (ESI) Data for Example 1 | | | | | | | | |
|---|---|---|---|---|---|---|---|---|---|
| | Prp 27-30 Control | | | | Prp 27-30 BS3 Dimer | | | Prp 27-30 BS3 Monomer | |
| peptide | MW theory | MW expt'l | error (ppm) | relative int | MW expt'l | error (ppm) | relative int | MW expt'l | error (ppm) | relative int |
| 90-106 | 1819.91 | 1819.94 | 15 | 33% | 1819.90 | 6 | 11% | 1819.90 | 7 | 27% |
| 111-136 | 2362.13 | 2362.14 | 3 | 62% | 2362.16 | 9 | 19% | 2362.15 | 7 | 45% |
| 137-148 | 1533.61 | 1533.56 | 33 | 100% | 1533.59 | 15 | 100% | 1533.57 | 26 | 82% |
| 157-164 | 1101.52 | 1101.50 | 22 | 18% | 1101.50 | 19 | 45% | 1101.51 | 18 | 36% |
| 165-185 | 2531.19 | 2531.20 | 3 | 1% | 2531.19 | 1 | 3% | 2531.22 | 14 | 3% |
| 186-194 | 1015.53 | 1015.55 | 20 | 2% | 1015.53 | 3 | 1% | 1015.53 | 3 | 1% |
| 186-204 | 2150.05 | 2150.04 | 5 | 0% | 2150.03 | 10 | 2% | 2150.05 | 2 | 2% |
| 195-204 | 1152.53 | 1152.51 | 18 | 4% | 1152.52 | 6 | 13% | 1152.53 | 4 | 15% |
| 209-220 | 1513.69 | 1513.67 | 17 | 55% | 1513.66 | 18 | 64% | 1513.67 | 17 | 100% |
| 221-229 | 1087.46 | 1087.48 | 21 | 3% | 1087.44 | 17 | 5% | 1087.45 | 5 | 6% |
| 221-230 | 1243.56 | 1243.58 | 21 | 3% | 1243.54 | 14 | 7% | 1243.55 | 11 | 10% |

Figure 3:
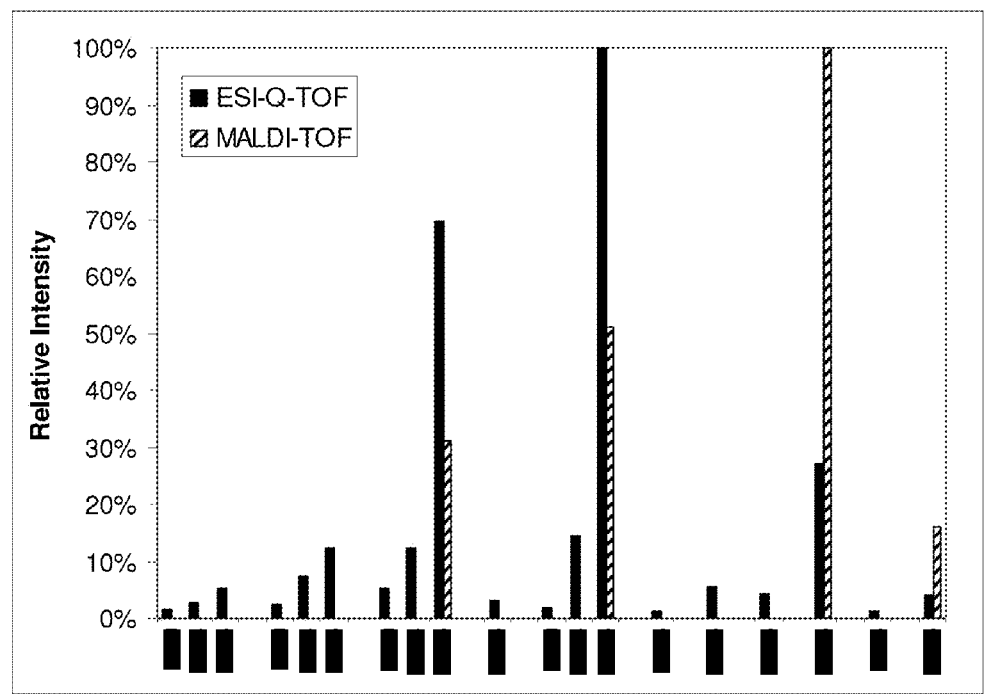
FIG. 3 shows comparison of the relative intensities of amino terminal tryptic peptides from PrP 27-30 identified by MALDI-TOF or nanoLC-ESI-Q-TOF mass spectrometry.

Proteolytic activity of proteinase K used during purification of PrP 27-30 generates a mixture of amino-terminally truncated molecular species. Amino terminal peptides formed by tryptic digestion of these species were identified by MALDI-TOF and nanoLC-ESI-Q-TOF mass spectrometry. Relative abundances of these amino terminal tryptic peptides are shown in FIG. 3. Interpretation is somewhat complicated due to limited tryptic cleavage at 101K/102P and at 104K/105P. Analysis of the ESI data shows three abundant amino termini (GLY 82, GLY 86 and GLY 90), and several SDS-PAGE of cross-linked PRP 27-30) was 11 ppm. The identity of the indicated sequences was confirmed by MS-MS (data not shown). The collision-activated dissociation (CAD) spectra of modified peptide 90-106 clearly shows that suberic acid is linked via the amino terminus of the peptide and not via the epsilon-amino group of either LYS101, LYS104 or LYS106. These results demonstrate that GLY 82, GLY 86, GLY 90 and GLY 92 are accessible to the cross-linking reagent and thus must be on the surface of PrP 27-30 fibrils.

TABLE 3

Evidence of Reaction of the Amino Termini with BS3

| | | Prp 27-30 BS3 Dimer | | | Prp 27-30 BS3 Monomer | | |
|---|---|---|---|---|---|---|---|
| species | MW theory | MW expt'l | error (ppm) | relative int | MW expt'l | error (ppm) | relative int |
| (82-106) + $C_8H_{12}O_3$ | 2752.32 | 2752.31 | 5 | 11% | 2752.37 | 16 | 18% |
| (86-106) + $C_8H_{12}O_3$ | 2333.13 | — | — | 0% | 2333.15 | 11 | 44% |
| (90-106) + $C_8H_{12}O_3$ | 1975.99 | 1975.97 | 9 | 30% | 1975.97 | 9 | 92% |
| (92-110) + $C_8H_{12}O_3$ | 2265.13 | 2265.17 | 15 | 34% | — | — | 0% |
| (90-106) + (90-106) + $C_8H_{10}O_2$ | 3777.88 | 3777.83 | 16 | 62% | — | — | 0% |
| (90-106) + (86-101) + $C_8H_{10}O_2$ | 3597.70 | 3597.72 | 6 | 12% | — | — | 0% |
| (90-106) + (90-104) + $C_8H_{10}O_2$ | 3552.74 | 3552.72 | 4 | 85% | — | — | 0% |
| (90-106) + (90-101) + $C_8H_{10}O_2$ | 3240.56 | 3240.56 | 2 | 100% | — | — | 0% |
| (91-106) + (92-101) + $C_8H_{10}O_2$ | 2998.45 | 2998.43 | 8 | 59% | — | — | 0% |

Figure 4:
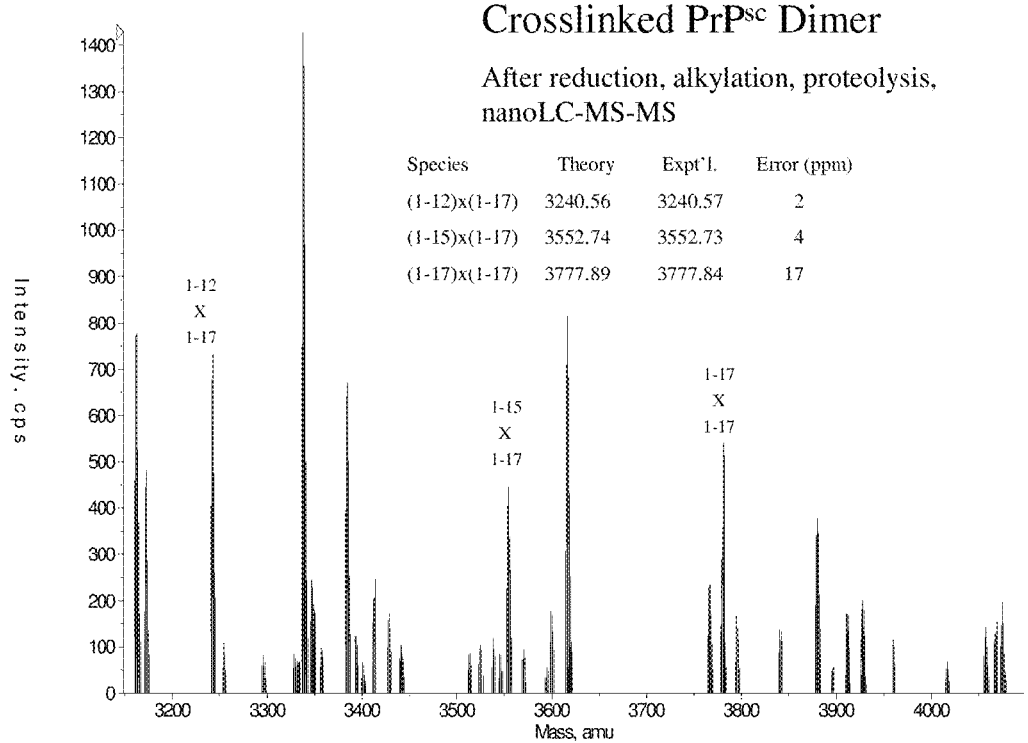
FIG. 4 shows detection of cross-linked peptides in trypsin digests of $BS^3$-cross-linked PrP 27-30 by nanoLC/MS.
Figure 5:
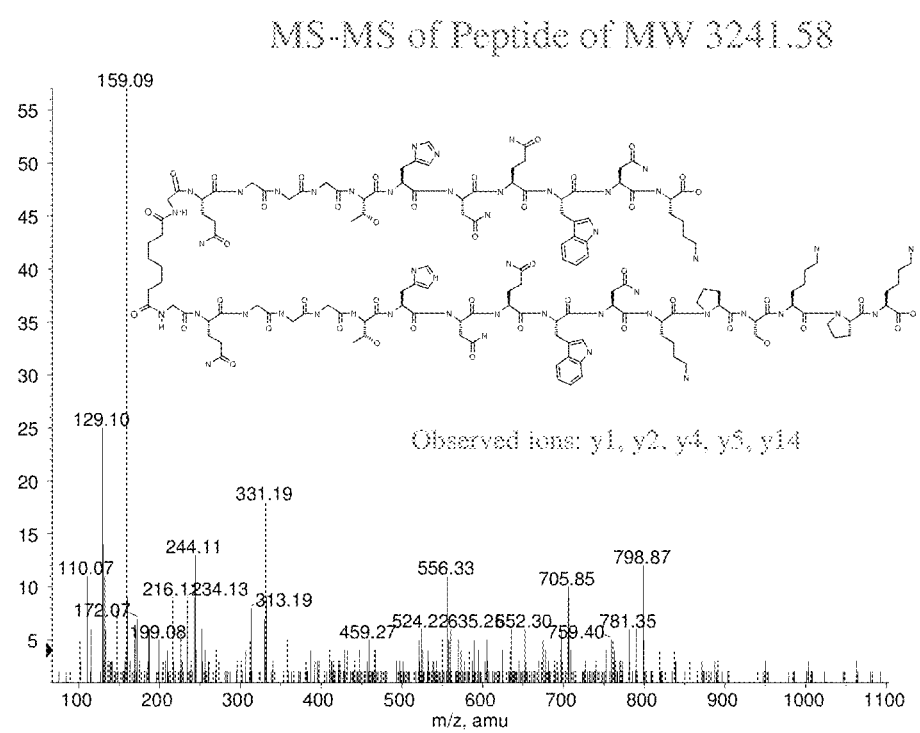
FIG. 5 shows confirmation of an intermolecular cross-link involving two $G_{90}$ amino termini in cross-linked PrP27-30 by MS/MS.

Five intermolecular crosslinked species were also found (Table 3, FIG. 4) in the dimer bands from SDS-PAGE. None were found in the control or monomer bands, as expected. Three of the intermolecular crosslinks arise by crosslinking two PrP 27-30 monomers which both have GLY 90 amino termini; the three species observed differ in the location of their carboxy termini due to limited tryptic cleavage at 101K/102P and at 104K/105P. The other intermolecular crosslinked species arise from crosslinking PrP 27-30 monomers with amino termini at GLY 90 and GLY 86, or from crosslinking PrP 27-30 monomers with amino termini at GLY 92 and GLY 91, respectively. Due to the difficulty of obtaining good quality MS-MS on small amounts of relatively large molecules (MWs 3,000-4,000), only the most abundant crosslink corresponding to (90-106)+(90-101)+$C_8H_{10}O_2$ could be confirmed by MS-MS (FIG. 5). Fragmentation observed is fully consistent with the proposed structure.

Figure 6:
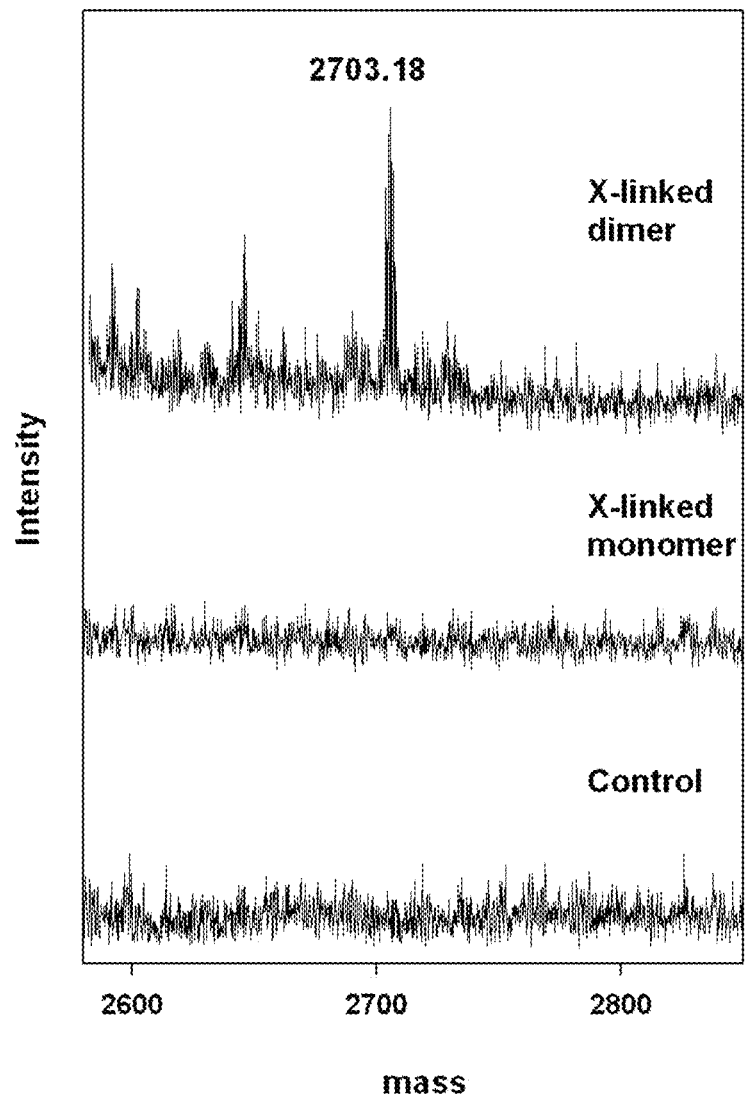
FIG. 6 shows detection of a cross-linked peptide, $G_{90}$-$K_{101}$-X-$G_{90}$-$K_{101}$, in the lysC digest of $BS^3$-cross-linked PrP 27-30 by MALDI-TOF. Bands were excised from gels and digested in gel with lysC overnight at 37° C. Peptides were extracted, dried in vacuo and analyzed by MALDI-TOF as described in Example 1, below.

Analysis of the dimer sample by MALDI confirmed the existence of the intermolecular species that is formed by crosslinking two PrP 27-30 monomers which both have GLY 90 amino termini. The evidence was a peak of MW=2703.18 (theoretical mass 2703.23, error=18 ppm), corresponding to an inter-molecular cross-link involving two (90-101) amino terminal peptides, seen in the lysC digest of cross-linked dimeric samples, but not in cross-linked monomers or controls (FIG. 6).

The observation of unmodified amino-terminal peptides (Table 2), and their suberic acid amides (Table 3) in the tryptic digests of crosslinked PrP 27-30 dimers, infers that some of the dimers are crosslinked at sites other than via their amino termini. Comparing the relative abundance of the 90-106 amino-terminal peptide in the PrP 27-30 control digest (33% of base peak intensity) to that found in the crosslinked PrP 27-30 dimer digest (11% of base peak intensity) suggests that as much as 33% of the crosslinked dimers have at least one free amino terminus, and must be crosslinked at sites undetected in this study. The detection of trimers and higher order oligomers in the reaction mixtures substantiates this conclusion.

Example 2

The following example describes differentiation of the two prion conformers, PrP$^C$ and PrP$^{Sc}$ in accordance with the methods of the invention, and wherein a monofunctional reagent (also denoted as a monodentate reagent) is used.

Materials and Methods
Reagents

Trypsin (sequencing grade, modified) was purchased from Promega (Madison, Wis.). Recombinant Syrian hamster prion protein (residues 90-231) was obtained from InPro Biotechnology (South San Francisco, Calif.). All other reagents were from SIGMA-ALDRICH®.

PrP 27-30 was isolated as described (Diringer et al. (1997)) from brains of terminally ill Syrian hamsters infected with the 263K strain of scrapie. Its purity and approximate concentration was assessed by SDS-PAGE and Coomassie blue staining. PrP 27-30 was suspended immediately before use in 1% sarkosyl at an approximate concentration of 0.1 μg/μl by vigorously vortexing to achieve a homogeneous suspension prior to use.

Monofunctional Derivatization

Reactions contained 1 μg of protein in 30 μl of 130 mM phosphate buffer, pH=7.4. Acetic anhydride was added from a freshly prepared stock solution in 20 mM phosphate buffer, pH=7.4, to a final concentration of 7 mM. Reaction was carried out at RT for 15 min and was then quenched by addition of trifluoroacetic acid (TFA) to 1% (v/v) and allowed to incubate at RT for an additional 10 minutes.

Precipitation and Electrophoretic Separation

Protein was precipitated with ice-cold methanol at a final concentration of 85%. The sample was spun in a table-top centrifuge at 14,000 rpm for 20 minutes and the supernatant discarded. The pellet was dissolved in reducing Laemmli buffer, boiled for 10 minutes and subjected to SDS-PAGE (Laemmli (1970)) using 15% gels. Protein bands were stained with Coomassie blue.

In-Gel Proteolytic Digestion

Protein bands were carefully excised with a razor blade, and then reduced, alkylated and digested in-gel with trypsin at an approximate mass ratio of 1:10 trypsin to PrP, according to the procedure of Shevchenko et al. (Shevchenko et al. (1996)) with slight modifications. Briefly, bands were cut to 1 mm³ pieces, placed in a micro centrifuge tube, washed with water and dehydrated with 200 μl acetonitrile for 15 minutes using mild agitation. Acetonitrile was removed and the gel pieces were dried in vacuo (SpeedVac, Savant, Farmingdale Calif.); a volume of 30 μl of 10 mM DTT in 25 mM $NH_4HCO_3$ was added and the reduction was carried out at 56° C. for 30 minutes. The solvent was then removed, and after dehydration of gel pieces with acetonitrile as described, replaced with 30 μl of 55 mM iodoacetamide. Alkylation was carried on in the dark at RT for 20 minutes. The solvent was then removed and gel pieces were washed with 25 mM $NH_4HCO_3$, dehydrated with acetonitrile and rehydrated on ice by addition of 20 μl of 25 mM $NH_4HCO_3$ containing 10 ng/μl trypsin. After 40 minutes, 30 μl of 25 mM $NH_4HCO_3$ were added to cover the gel pieces and samples were incubated overnight at 37° C. Digested samples were briefly centrifuged and the supernatant collected. Gel pieces were then extracted with 20 μl of 25 mM NH$_4$HCO$_3$ with sonication for 10 minutes. The solvent was then recovered and replaced with 20 μl of 0.1% trifluoroacetic acid (TFA). The extracts and the digestion solution were pooled and dried in vacuo by centrifugal evaporation (Speed-Vac, Savant).

Nanospray LC/MS/MS

Protein digests were redissolved in 10 μl of 50% acetonitrile containing 1% formic acid, sonicated for 10 min, then diluted with 40 μL of 1% aq. formic acid. NanoLC-ESI-MS-MS was done with an Applied Biosystems (ABI/MDS Sciex, Toronto, Canada) Model QStar Pulsar equipped with a Proxeon Biosystems (Odense, Denmark) nano-electrospray source. In-gel digest (20 μl) was loaded automatically onto a C-18 trap cartridge and chromatographed on a reversed-phase column (Vydac 238EV5.07515, 75μ×150 mm; Hesperia, Calif.) fitted at the effluent end with a coated spray tip (FS360-50-5-CE, New Objective Inc., Woburn, Mass.). An LC Packings nano-flow LC system (Dionex, Sunnyvale, Calif.) with autosampler, column switching device, loading pump, and nano-flow solvent delivery system was used to elute the column. Elution solvents were: A (0.5% acetic acid in water) and B (80% acetonitrile, 0.5% acetic acid). Samples were eluted at 250 nl/min with the following gradient profile: 2% B at 0 min to 80% B in a 30 min linear gradient; held at 80% B for 5 min then back to 2% B for 10 min. The QStar Pulsar was externally calibrated daily and operated above a resolution of 8,000. The acquisition cycle time of 6 s consisted of a single is MS "survey" scan followed by a 5 s MS/MS scan. Ions between m/z 400 to 1,000 of charge states between +2 to +5 having intensities greater than 40 counts in the survey scan were selected for fragmentation. The dynamic exclusion window was set to always exclude previously fragmented masses. Collision energy optimized for charge state and m/z was automatically selected by the Analyst QS software after adjusting parameters to obtain satisfactory fragmentation of GLU fibrinogen peptide (+2), and ACTH (+3 and +4). Nitrogen was used for the collision gas and the pressure in the collision cell ranged from 3×10-6 to 6×10-6 ton.

Data Analysis

To assist in assignment of unmodified peptides present in the digest the MSMS data was submitted to Mascot (Matrix Science). For these peptides an RMS mass error of 20-30 ppm was observed. Next, the TOF-MS survey scans were processed with the "LCMS Reconstruct" tool in the Analyst software. The output is a list of peptide molecular weights calculated by deconvolution of multiple charge states and then identification of the monoisotopic $^{12}$C species. The data was then searched manually to find peptides modified by acetic anhydride. MSMS of relevant peaks was also interpreted manually.

Results

Treatment of PrP 27-30 or recombinant PrP 90-231 (rPrP90-231) with acetic anhydride resulted in differentially modified protein products. Tryptic digests of PrP 27-30, or recombinant PrP 90-231 after reaction with acetic anhydride were analyzed by nanoLC-ESI-Q-TOF mass spectrometry and were found to contain modified peptides, some of which were unique to each protein conformer. The ESI data are summarized in Table 4. Four classes of peptides were found. Two examples of each are described.

Class 1. Peptides unique to PrP$^{Sc}$: Examples shown are 1-17 having reacted once with acetic anhydride and 1-17 unmodified. MSMS of 1-17 conclusively shows the site of modification to be at Gly1, the amino terminal amino acid.

Class 2. Peptides unique to PrP$^C$: Examples shown are 97-115 having reacted once with acetic anhydride, and 106-119 having reacted once with acetic anhydride and found as the methionine sulfoxide (a common oxidation product of methionine often observed in proteins purified by SDS-PAGE). MSMS data of these peptides conclusively shows that the epsilon-amino group of the internal lysine residues (Lys105 for 97-115, and Lys115 for 106-119) are the sites of acetylation.

Class 3. Modified peptides found in both PrP$^C$ and PrP$^{Sc}$ but in significantly different amounts. Examples shown are 1-17 having reacted twice with acetic anhydride and 1-17 having reacted three times with acetic anhydride. MSMS data of 1-17 having reacted two times with acetic anhydride clearly shows the sites of modification at Gly1 (the amino terminus) and Lys12, but not at Lys15 or Lys17. MSMS data of 1-17 having reacted three times with acetic anhydride clearly shows the sites of modification at Gly1 (the amino terminus), Lys12 and Lys15, but not at Lys17.

Class 4. Peptides found in both PrP$^C$ and PrP$^{Sc}$ but in essentially the same amount. Examples shown are 48-59 and 68-75. Both these peptides have carboxy-terminal arginines, are preceded by arginine, and contain no residues likely react with acetic anhydride.

RMS mass error for the peptides listed in Table 4 is 25 ppm which is consistent with the range of errors observed for the entire set of unmodified peptides (see above). The identity of all the peptides listed in Table 4 (with the exception of unmodified 1-17 which co-eluted with more abundant peaks) was confirmed by MS-MS (data not shown).

TABLE 4

Electrospray Ionization (ESI) Data for Example 2

| peptide | modifications | MW theory | Peptides from recombinant PrP | | | Peptides from PrP 27-30 | | |
|---|---|---|---|---|---|---|---|---|
| | | | MW expt'l | error (ppm) | rel intensity | MW expt'l | error (ppm) | rel intensity |
| 1-17 | none | 1819.91 | — | — | 0 | 1819.84 | 37 | 11 |
| 1-17 | Ac_1 | 1861.92 | — | — | 0 | 1861.84 | 44 | 4 |
| 1-17 | Ac_2 | 1903.93 | 1903.90 | 13 | 3 | 1903.86 | 38 | 33 |
| 1-17 | Ac_3 | 1945.94 | 1945.91 | 14 | 14 | 1945.96 | 11 | 1 |
| 97-115 | Ac_1 | 2192.06 | 2192.04 | 8 | 4 | — | — | 0 |
| 106-119 | 1 oxygen and Ac_1 | 1739.80 | 1739.77 | 19 | 26 | — | — | 0 |
| 48-59 | 2 oxygens | 1565.60 | 1565.57 | 22 | 100 | 1565.54 | 38 | 100 |
| 68-75 | none | 1101.52 | 1101.50 | 21 | 38 | 1101.48 | 41 | 33 |

Modification "Ac_x" refers to the indicated peptide having reacted x times with acetic anhydride.

Example 3

The following example illustrates an exemplary method for obtaining proteinase K (PK) sensitive fraction and the PK resistant fraction PrP$^{Sc}$. This material can be isolated by a modified version of the method Diringer et. al. (1997) *Intervirology* 40:238-246.

Each infected hamster brain was homogenized in 12.5 ml of homogenization buffer (10% solution of Sarcosyl, 9.5 mM sodium phosphate, pH 8.5, and 1% volume of Protease inhibitor cocktail; SIGMA®Life Sciences). After homogenization, the homogenate was allowed to stand for 30 minutes at room temperature. After standing for 30 minutes, the homogenate was transferred to Beckman quick-seal poylallomer centrifuge tubes (16×76 mm).

The tubes were balanced, sealed and centrifuged at 20° C. for 18 minutes at 16,000×g (Beckman L8 70M ultracentrifuge; Ti 70.1 Ti rotor) to remove large particulates. The supernatant was removed and a concentrated EDTA (pH 7.6) solution was added to make final concentration of 8 mM EDTA in 12.5 mL of homogenization buffer. The 12.5 mL homogenization buffer containing EDTA was added to fresh Beckman quick-seal poylallomer centrifuge tubes (16×76 mm). The homogenization buffer was underlain with 1 ml of 20% (w/v) aqueous sucrose solution. The tubes were balance, sealed, and the sample was centrifuged at 20° C. for 97 minutes at 145,000×g (Beckman L8 70M ultracentrifuge; Type 70.1 Ti rotor). The supernatant was removed to yield a pellet that contains both the PK resistant and PK sensitive forms of PrP$^{Sc}$.

Obtaining PrP27-30. The previously described pellet is resuspended in a small volume of buffer (20 mM Tris/HCl Ph 8.5; containing 1% w/v Sarkosyl). The pellet is homogenized by applying sonication (4×45 sec pulse; Misonix 300 w/microplate horn) to the sample. The homogenized pellet is treated with PK (50 μg/mL) for 1 h at 37° C. Proteolysis is halted by the addition of protease inhibitors (1% volume Protease inhibitor cocktail; SIGMA®Life Sciences) to yield PrP27-30.

PK resistant $PrP^{Sc}$ is obtained by the method of Pastrana et. al. (Pastrana M A, Sajnani G, Onisko B, Castilla J, Morales R, Soto C, Requena J R. Isolation and characterization of a proteinase K-sensitive PrPSc fraction. Biochemistry. 2006 Dec. 26; 45(51):15710-7.) The previously described, non PK treated, pellet is resuspended in a small volume of buffer (20 mM Tris/HCl Ph 8.5; containing 1% w/v Sarkosyl) and sonicated (3 to 4×1 sec pulses; amplitude 50%; Cole Parmer 4710 Ultrasonics homogenizer with a 4710 series probe). The sonicated pellet was resuspended in enough buffer (20 mM Tris/HCl Ph 8.5; containing 1% w/v Sarkosyl) to fill 0.5 mL Beckman quick-seal poylallomer centrifuge tubes (8×34 mm). The tubes were balanced, sealed, and centrifuged (Beckman Optima TLX personal micro-ultracentrifuges; TLA-120.1 rotor) at 20° C. for 2 hours at 56,000×g. The supernatant was removed and saved. The pellet contains PK resistant $PrP^{Sc}$.

PK sensitive $PrP^{Sc}$ is obtained by the method of Pastrana et. al. The supernatant from the isolation of the PK resistant $PrP^{Sc}$ contains the PK sensitive $PrP^{Sc}$.

$PrP^{C}$ can be isolated by the method Pergami et. al. [Pergami P, Jaffe H, Safar J. Semipreparative chromatographic method to purify the normal cellular isoform of the prion protein in nondenatured form. Anal Biochem. 1996 Apr. 5; 236(1):63-73.]. Forty grams of hamster brains were homogenized in 200 mL of buffer (0.32 M sucrose, 0.5 mM KCl, 1 mM $MgCl_2$, 5 mM PMSF, 1 mM DTT; 0° C.). The homogenate was centrifuged at 4° C. for 10 minutes at 3000×g (Eppendorf 5810R centrifuge; A-4-81 rotor). The supernatant was saved and the pellet was homogenized in 170 mL of buffer (0.32 M sucrose, 0.5 mM KCl, 1 mM $MgCl_2$, 5 mM PMSF, 1 mM DTT; 0° C.). The rehomogenized pellet was centrifuged at 4° C. for 10 minutes at 3000×g (Eppendorf 5810R centrifuge; A-4-81 rotor). This supernatant was mixed with the previous supernatant. The combined supernatants were transferred to pre cooled (4° C.) Beckman quick-seal poylallomer centrifuge tubes (25×896 mm) containing 15 mL of 0.85 M sucrose. The tubes were balanced, sealed, and ultracentrifuged at 4° C. for 1 hour at 100,000×g (Beckman L8 70M ultracentrifuge; Type 70 Ti rotor). The supernatant was discarded.

The pellet was resuspended in buffer containing a non-denaturing detergent (MES 12.5 mM, Tris 12.5 mM, NaCl 50 mM, pH 7.5, 2% w/v β-octylglucopyranoside) by gentle stirring at room temperature for 30 minutes. Buffer (MES 12.5 mM, Tris 12.5 mM, NaCl 50 mM, pH 7.5, 2% w/v β-octylglucopyranoside) was added until the final protein concentration of protein reached 1.36 mg/mL. The resuspended buffer was transferred into fresh Beckman quick-seal poylallomer centrifuge tubes (25×896 mm). The tubes were balanced, sealed and ultracentrifuged at 15° C. for 1 hour at 100,000×g (Beckman L8 70M ultracentrifuge; Type 70 Ti rotor).

The pellet was discarded and the supernatant was diluted with buffer (MES 12.5 mM, Tris 12.5 mM, NaCl 50 mM, pH 7.5) to yield a solution containing 30 mM β-octylglucopyranoside. The resulting solution was filtered through a 0.2 micron filter and subjected to cation-exchange chromatography (TSK-SP-5PW column (150 mm×21.5 mm); gradient: starting: MES 12.5 mM, Tris 12.5 mM, NaCl 150 mM, pH 7.5, β-octylglucopyranoside 30 mM; ending: MES 12.5 mM, Tris 12.5 mM, NaCl 500 mM, pH 7.5, β-octylglucopyranoside 30 mM; 120 min run; flow rate 4 mL/min). The fractions containing $PrP^{C}$ (Western blot; 3F4 antibody) were concentrated (Centriprep 30; Amicon).

NaCl and imidazole were added to the concentrated $PrP^{C}$ sample to yield a final buffer concentration of MES 12.5 mM, Tris 12.5 mM, NaCl 500 mM, imidazole 0.5 mM, β-octylglucopyranoside 30 mM, pH 7.5. This reconstituted $PrP^{C}$ sample was subjected to immobilized metal-affinity HPLC (MC-POROS100×4.6 mm; PerSeptive Biosystems; Cobalt cation; step gradient; initial step: MES 12.5 mM, Tris 12.5 mM, NaCl 500 mM, imidazole 0.5 mM, β-octylglucopyranoside 30 mM, pH 7.5; flow rate 3 mL/min; 2 min; final step: MES 12.5 mM, Tris 12.5 mM, NaCl 500 mM, imidazole 20 mM, β-octylglucopyranoside 30 mM, pH 7.5; flow rate 3 mL/min; 10 min). The fractions containing $PrP^{C}$ (Western blot; 3F4 antibody) were concentrated and subjected to size exclusion chromatography (Toro-Haas TSK G3000SW, HPLC column (600×17.5 mm i.d., Thompson Scientific; Elution buffer: Mes 12.5 mM, Tris 12.5 mM, NaCl 500 mM, β-octylglucoside 30 mM, pH 7.5; flow rate 0.5 ml/min). Those fractions containing PrPC were collected and determined to be >90%.

Example 4

Creation of Amide Bonds Using an Activated Ester 1-fluoro-2,4-dinitrobenzene (FDNB) (Sanger's Reagent)

Reaction Conditions:

The isolated conformers were redissolved in aqueous buffer at a pH in the range (using MOPS, MES, trimethyl amine, triethylamine, Phosphate, etc.) from 6.0 to 9.0. To this solution was added a solution of 1-fluoro-2,4-dinitrobenzene (FDNB) (Sanger's reagent) dissolved in a small volume N,N- dimethylformamide (DMF). The reaction was allowed to proceed for 1 hr at pH 7.0 or overnight at pH 8.0. The reaction mixture was extracted with diethylether to remove unreacted FNDB. The reacted protein is purified by standard protein purification techniques (e.g., size exclusion chromatography, reverse phase chromatography, SDS-PAGE) to yield a protein that is suitable for inoculation into mice to yield antibodies.

Alternately, the purified protein can be analyzed by mass spectrometry to determine the chemical nature of the modification. A synthetic version of the peptide can be prepared using standard solid-phase peptide synthesis. The peptide can be covalently attached to carrier proteins such as keyhole limpet hemocyanin, bovine serum ablumin or other appropriate carrier. The carrier can be used to inoculate mice to generate antibodies specific to the modified peptide fragment.

Example 5

Example: Acetic Acid NHS Ester

The isolated conformers were redissolved in aqueous buffer containing (4-(2-hydroxyethyl)-1-piperazineethanesulfonic acid) (HEPES) at a pH of 7.7. The NHS ester of acetic acid was dissolved in DMSO. A 10-400 molar excess of the HNS acetic acid ester was added and allowed to react for at least 1 hour. The reaction was quenched with an excess of ammonium acetate. The protein was purified and used to create antibodies or to identify the nature of the modification.

Example 6

Example: Carboxylic Acid, 1-ethyl-3-(3-dimethylaminopropyl)carbodiimide hydrochloride (EDC) and N-hydroxysulfosuccinimide (Sulfo-NHS). [Staros J V, Wright R W, Swingle D M. Enhancement by N-hydroxysulfosuccinimide of Water-Soluble Carbodiimide-Mediated Coupling Reactions. Anal. Biochem. 1986; 156: 220-222.]

The isolated conformers were redissolved in aqueous buffer containing 5 mM sodium phosphate at a pH 7.4. The carboxylic acid and Sulfo-HNS were added to a 10-400 molar excess. A sufficient quantity of EDC was added to make a 100 mM solution. The reaction was allowed to continue to completion. The reaction was quenced by the addition of ammoniumacetate. The resulting protein was purified and used to crete antibodies or to identify the nature of the modification, which could be used to synthesize peptides for the creation of antibodies.

Example 7

Example Acetic Acid Sulfo-NHS Ester

The isolated conformers were redissolved in aqueous buffer containing (4-(2-hydroxyethyl)-1-piperazineethanesulfonic acid) (HEPES) at a pH of 7.7. The Sulfo-NHS ester of acetic acid was added to a 10-400 molar excess. The reaction was allowed to proceed to completion at 4° C. at least 1 hour. The reaction was quenched with an excess of ammonium acetate at 4° C. The protein was purified and used to create antibodies or to identify the nature of the modification.

Example 8

The following example illustrates the detection of PrPSc using monoclonal antibodies prepared according to the methods disclosed herein.

A person of skill in the art acquires an appropriate tissue sample from an animal (e.g. sheep, goat, deer, elk, moose, domestic cattle). The sample is homogenized in an appropriate buffer (e.g. proper pH [6.0-10.0], appropriate buffer [contains no primary or secondary amines], etc.). The homogenate is centrifuged at low speed to remove large particulates that may interfere with subsequent analysis.

The appropriate reagent (e.g. FDNB) is added to the homogenate at the appropriate concentration and allowed to react for the appropriate length of time. The reagent would be quenched in the prescribed fashion.

The homogenate now contains covalently modified forms of $PrP^{Sc}$ and $PrP^C$. The covalently modified version of $PrP^{Sc}$ will react with the antibody, but not the unmodified $PrP^C$. The antibody is used to distinguish between the two by the intensity of the signal.

The homogenate is run on a SDS-PAGE get and transferred to a nitrocellulose or polyvinylidene Fluoride (PVDF) membrane. The membrane containing the transferred proteins is then analyzed by western blot. The produced antibodies would be the primary antibody and would only bind to the chemically modified $PrP^{Sc}$ and not the unmodified $PrP^C$. Only those samples containing the modified $PrP^{Sc}$ would yield a signal. Those samples containing only $PrP^C$ would produce no signal.

The homogenate could be analyzed in an analogous fashion using ELISA, sandwich ELISA, ELISA-based dipstick, etc. The homogenate or concentrate would have to be denatured in guanidine to expose the modified epitope present in $PrP^{Sc}$. The guanidine would have to be diluted to minimize its effect on subsequent reactions. Again the signal would only result if $PrP^{Sc}$ present. Since $PrP^C$ is not recognized by the antibody, it would produce no signal.

Example 9

A person of skill acquires an appropriate tissue sample from an animal (e.g. sheep, goat, deer, elk, moose, domestic cattle). The sample would need to be homogenized in an appropriate buffer (e.g. proper pH [6.0-10.0], appropriate buffer [contains no primary or secondary amines], etc.). The homogenate is centrifuged at low speed to remove large particulates that may interfere with subsequent analysis. The appropriate reagent (e.g. FDNB) would be added to the homogenate at the appropriate concentration and allowed to react for the appropriate length of time. The reagent would be quenched in the prescribed fashion.

The homogenate now contains covalently modified forms of $PrP^{Sc}$ and $PrP^C$. Since $PrP^C$ is modified by the reagent, but not $PrP^{Sc}$, either known antibodies can be used or antibodies developed to specific unmodified haptens have been developed.

PrPSc can be concentrated by ultracentrifugation or by using phosphotungstic acid (PTA) concentration. The resulting $PrP^{Sc}$ would contain modified $PrP^C$. The resulting concentrates could be run on a SDS-PAGE gel and transferred to a nitrocellulose or Polyvinylidene Fluoride (PVDF) membrane. The membrane containing the transferred proteins could be analyzed by western blot. The produced antibodies would be the primary antibody and would only bind to the unmodified $PrP^{Sc}$ and not the covalently modified $PrP^C$. Only those samples containing un modified $PrP^{Sc}$ would yield a signal. Those samples containing only $PrP^C$ would produce no signal.

The homogenate could be analyzed in an analogous fashion using ELISA, sandwich ELISA, ELISA-based dipstick, etc. The homogenate or concentrate would have to be denatured in guanidine to expose the unmodified epitope present in PrP$^{Sc}$. The guanidine would have to be diluted to minimize its effect on subsequent reactions. Again the signal would only result if PrP$^{Sc}$ was present. The presence of chemically modified PrP$^C$ would not be detected by the antibody, so there would be no signal.

It is understood that the foregoing detailed description is given merely by way of illustration and that modification and variations may be made within, without departing from the spirit and scope of the invention. All publications and patents cited herein are hereby incorporated by reference in their entirety.

(iii) reacting each conformationally distinct population of macromolecules with a covalent modifier which binds differentially to each of the stable macromolecule conformations, thereby providing covalently modified macromolecules which comprise newly created epitopes, wherein the newly created epitope comprises at least one bound covalent modifier;

(iv) immunizing a laboratory animal;

(v) monitoring the immune response to the immunogen preparation to determine a titer of antibodies to the newly created epitopes;

---

---

We claim:

1. A method for preparing monoclonal antibodies that are capable of discriminating between at least two stable macromolecular conformations of a macromolecule, the method comprising:
   (i) isolating a population of macromolecules wherein the population of macromolecules comprises the at least two stable macromolecule conformations of the macromolecule, wherein the at least two stable macromolecule conformations of the macromolecule possess physical differences which allow the at least two stable macromolecule conformations to be separated from each other;
   (ii) separating the at least two stable macromolecule conformations from one another to provide at least two distinct homogeneous populations of purified macromolecules wherein each population is conformationally distinct from one another;

(vi) collecting blood comprising the antibodies to the newly created epitope;
   (vii) preparing antisera; and
   (viii) fractionating the antisera to enrich for antibodies reactive to the newly created epitopes;
   thereby preparing antibodies that selectively bind to the newly created epitopes and thus are capable of discriminating between at least two stable macromolecular conformations of a macromolecule.

2. The method of claim 1, wherein the method further comprises:
   prior to step (iv) fragmenting the covalently modified macromolecules which comprise newly created epitopes to provide macromolecule fragments comprising the newly created epitopes.

3. The method of claim 1, wherein the macromolecule is a prion protein.

4. A method for increasing the sensitivity of detection of a macromolecular conformation of a macromolecule, wherein the macromolecule has at least two stable macromolecular conformations, the method comprising:

(i) preparing monoclonal antibodies that are capable of discriminating between at least two stable macromolecular conformations of a macromolecule by (a) isolating a population of macromolecules wherein the population of macromolecules comprises the at least two stable macromolecule conformations of the macromolecule, and wherein the at least two stable macromolecule conformations of the macromolecule possess physical differences which allow the at least two stable macromolecule conformations to be separated from each other;

(b) separating the at least two stable macromolecule conformations from one another to provide at least two distinct homogeneous populations of purified macromolecules wherein each population is conformationally distinct from one another;

(c) reacting each conformationally distinct population of macromolecules with a covalent modifier which binds differentially to each of the stable macromolecule conformations, thereby providing covalently modified macromolecules which comprise newly created epitopes, wherein the newly created epitope comprises at least one bound covalent modifier;

(d) immunizing a laboratory animal;

(v) monitoring the immune response to the immunogen preparation to determine a titer of antibodies to the newly created epitopes;

(vi) collecting blood comprising the antibodies to the newly created epitope;

(vii) preparing antisera; and (viii) fractionating the antisera to enrich for antibodies reactive to the newly created epitopes;

thereby preparing antibodies that selectively bind to the newly created epitopes and thus are capable of discriminating between at least two stable macromolecular conformations of a macromolecule;

(ii) selecting an antibody capable of selectively binding to a newly created epitope unique to the protein conformer the increased sensitivity of which is desired thereby designating a chosen antibody;

(iii) preparing a biological sample by reacting the biological sample with a covalent modifier to produce a prepared biological sample;

(iv) reacting the chosen antibody with the prepared biological sample to obtain a detection result with increased sensitivity of detection for a macromolecular conformation of a macromolecule; and (v) interpreting the detection result.

5. The method of claim 4, wherein said sample is a biological tissue or fluid.

6. The method of claim 5, wherein said biological tissue or fluid is selected from the group consisting of brain, muscle, blood, tonsil, spleen, and lymph.

* * * * *